United States Patent
Ohta et al.

(10) Patent No.: US 9,050,278 B2
(45) Date of Patent: Jun. 9, 2015

(54) SCAVENGER OF IN VIVO HARMFUL REACTIVE OXYGEN SPECIES AND/OR FREE RADICALS

(71) Applicants: Shigeo Ohta, Kanagawa (JP); Wataru Murota, Ishikawa (JP); Ikuroh Ohsawa, Tokyo (JP)

(72) Inventors: Shigeo Ohta, Kanagawa (JP); Wataru Murota, Ishikawa (JP); Ikuroh Ohsawa, Tokyo (JP)

(73) Assignee: Shigeo Ohta, Kanagawa (JP)

( * ) Notice: Subject to any disclaimer, the term of this patent is extended or adjusted under 35 U.S.C. 154(b) by 0 days.

(21) Appl. No.: 13/759,300

(22) Filed: Feb. 5, 2013

(65) Prior Publication Data

US 2013/0177653 A1    Jul. 11, 2013

Related U.S. Application Data

(62) Division of application No. 12/848,431, filed on Aug. 2, 2010, now abandoned, which is a division of application No. 11/990,649, filed as application No. PCT/JP2006/316665 on Aug. 18, 2006, now abandoned.

(30) Foreign Application Priority Data

Aug. 19, 2005 (JP) .................................. 2005-238572
Jun. 6, 2006 (JP) .................................. 2006-157827

(51) Int. Cl.
*A61K 33/00* (2006.01)
*A23L 1/30* (2006.01)
*A23L 2/52* (2006.01)
*A23L 3/3427* (2006.01)

(52) U.S. Cl.
CPC . *A61K 33/00* (2013.01); *A23L 1/30* (2013.01); *A23L 2/52* (2013.01); *A23L 3/3427* (2013.01)

(58) Field of Classification Search
CPC .............................. A61K 2300/00; A61K 33/00
See application file for complete search history.

(56) References Cited

U.S. PATENT DOCUMENTS

| | | | |
|---|---|---|---|
| 6,623,615 | B1 | 9/2003 | Morisawa et al. |
| 2004/0154993 | A1 | 8/2004 | Yanagihara et al. |
| 2005/0224996 | A1 | 10/2005 | Yoshida |

FOREIGN PATENT DOCUMENTS

| | | |
|---|---|---|
| JP | 2000-517311 | 12/2000 |
| JP | 2002-172317 | 6/2002 |
| JP | 2002-301483 | 10/2002 |
| JP | 2003-10865 | 1/2003 |
| JP | 2003-19426 | 1/2003 |
| JP | 2003-170178 | 6/2003 |
| JP | 2004-122088 | 4/2004 |
| JP | 2004-174301 | 6/2004 |
| JP | 2005-082593 | 3/2005 |
| JP | 2005-87257 | 4/2005 |
| JP | 2005-218885 | 8/2005 |
| WO | 9204023 | 3/1992 |
| WO | 98/08523 | 3/1998 |
| WO | 2004-050563 | 6/2004 |

OTHER PUBLICATIONS

Das (Pathophysiology of Reperfusion Injury. CRC Press; Boca Raton, FL: 1993. pp. 1-14 and 31-34).*
Suzuki et al. (Japanese Journal of surgery 1983, 13 (6), 530-534).*
International Search Report issued Sep. 26, 2006 in International (PCT) Application No. PCT/JP2006/316665.
Chinese Office Action issued Feb. 5, 2010 in corresponding Chinese Application No. 2006800383430.
"Drink 'oxygen-rich water' for Oxygen Supplement"; Deep Frozen Technique; Jun. 1998; vol. 3; p. 25 (with English translation).
K. Kikuchi et al., "Hydrogen concentration in water from an Alkali-Ion-Water electrolyzer having a platinum-electroplated titanium electrode", Journal of Applied Electrochemistry (2001), vol. 31, pp. 1301-1306.
Extended European Search Report issued Jan. 2, 2012 in corresponding European Application No. 06796764.6.
Japanese Office Action issued Jan. 17, 2012 in corresponding Japanese Application No. 2007-531053, with English translation.
Gharib, Bouchra, et al., "Anti-inflammatory properties of molecular hydrogen: investigation on parasite-induced liver inflammation", Life Sciences, vol. 324, No. 8, Aug. 1, 2001, pp. 719-724.

(Continued)

*Primary Examiner* — Abigail Fisher
*Assistant Examiner* — Jessica Kassa
(74) *Attorney, Agent, or Firm* — Wenderoth, Lind & Ponack, L.L.P.

(57) ABSTRACT

An object of the present invention is to provide a scavenger of in vivo harmful reactive oxygen species and/or free radicals, which is capable of effectively reducing the concentrations of in vivo reactive oxygen species and/or free radicals and exhibiting given effects such as the suppression of aging process, the prevention of geriatric or lifestyle-related disease, health promotion, and the inhibition of oxidative stress by virtue of this reduction in the concentrations of reactive oxygen species and/or free radicals. The scavenger of in vivo harmful reactive oxygen species and/or free radicals of the present invention comprises a liquid or gas comprising at least a hydrogen molecule. This medium may further comprise an oxygen molecule. Furthermore, this medium may comprise water or an aqueous solution or may be a gas. The scavenger of reactive oxygen species and/or free radicals can be used in the treatment or prevention of a disorder attributed to reactive oxygen species and/or free radicals.

7 Claims, 40 Drawing Sheets

(56) References Cited

OTHER PUBLICATIONS

Hanaoka, K., "Antioxidant effects of reduced water produced by electrolysis of sodium chloride solutions", Journal of Applied Electrochemistry, vol. 31, No. 12, Dec. 2001, pp. 1307-1313.
Sun et al., Exp. Biol. Med., 2009, 234, pp. 1212-1219.
Fukuda et al., Biochemical and Biophysical Research Communications, 2007, 361, pp. 670-674.
Zheng et al., Free Radical Research, 2009, 43, pp. 478-484.
Gao, Journal of Pharmacology and Experimental Therapeutics, 2002, 301, pp. 543-550.

* cited by examiner (0 hour: addition of 30 μg/ml antimycin A to cells)

Untreated with hydrogen gas

Hydrogen gas inhaled

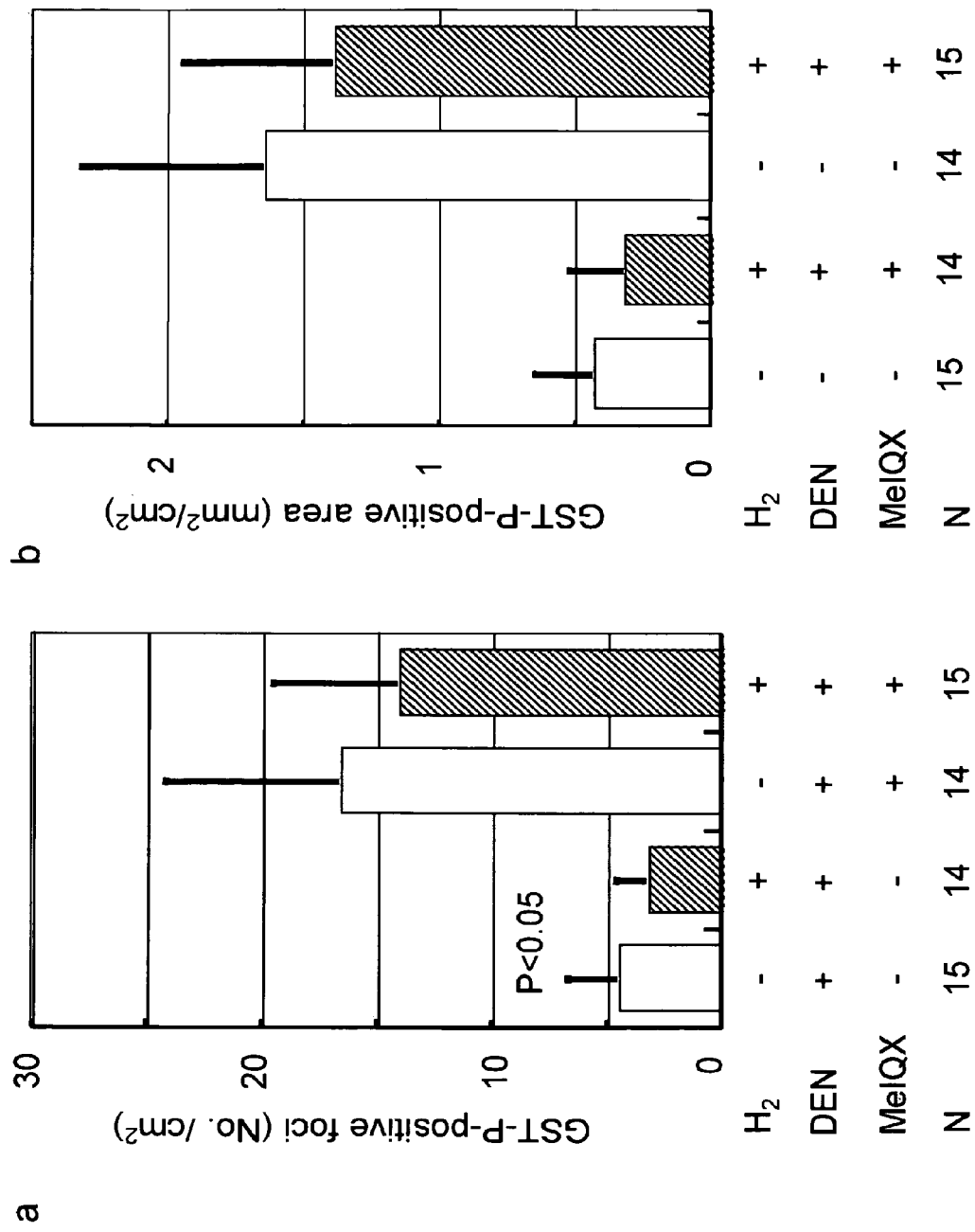

SCAVENGER OF IN VIVO HARMFUL REACTIVE OXYGEN SPECIES AND/OR FREE RADICALS

TECHNICAL FIELD

The present invention relates to a scavenger of reactive oxygen species and/or free radicals, which reduces the concentrations of in vivo harmful reactive oxygen species and/or free radicals. Particularly, the present invention relates to a scavenger of in vivo harmful reactive oxygen species and/or free radicals, which is capable of effectively reducing the concentrations of in vivo reactive oxygen species and/or free radicals and exhibiting effects such as the suppression of aging process, the prevention of geriatric or lifestyle-related diseases, health promotion, and the protection against oxidative stress.

BACKGROUND ART

It is now accepted widely that the presence of reactive molecules called reactive oxygen species or free radicals is generally at least one of causes of many human health abnormalities including aging, cancers, atherosclerosis, myocardial infarction, attacks, viral infections, lung abnormalities, bowel diseases, and neurodegenerative diseases and leads to aging and deterioration in health. These molecules, which are usual by-products of physiological reactions, are produced by enormous numbers of enzyme reactions indispensable to oxygen metabolism, for example, cellular respiration, or to the functions of the immune system (killing of foreign substances) and metabolism.

Particularly, mitochondria, subcellular organelles, transfer electrons in the electron transport system, while an electron leak always occurs. 2% to 0.2% of oxygen molecules used in respiration is reduced into reactive oxygen species. Furthermore, such reactive oxygen species are universally generated even in general environments. For example, ambient sources of reactive oxygen species encompass smoke, ionizing radiation, atmospheric pollution, chemical agents (carcinogens, many petrochemicals, biocides, dyes, solvents, cell division inhibitors, etc.), toxic heavy metals, and oxidized or rancid fats. Examples of the most general reactive oxygen species include superoxide radicals, hydroxyl radicals, singlet oxygen, and hydrogen peroxide. The reactive oxygen species encompass, in the broad sense, nitrogen monoxide, peroxynitrite, and lipid radicals such as alkoxyl radicals or lipid peroxyl radicals. For example, superoxide, hydroxyl radicals, nitrogen monoxide, and lipid radicals such as lipid peroxyl radicals or alkoxyl radicals are free radical molecules.

Free radical molecules have oxidative toxicity that causes structural damage to all biomolecules such as nucleic acids, proteins, and lipids in living organisms. Such molecular damage induces cellular abnormalities such as alteration in genetic codes, abnormalities in enzyme reactions, and lipid membrane degeneration and causes cytotoxicity. Thus, the free radical molecules have strong oxidizing power. A disorder caused by this oxidizing power is generally called oxidative stress. The accumulation of such oxidative stress may cause neurological disorders, endocrine disruption, increased allergy, vascular endothelial destruction, joint destruction, and inflammation at an individual level.

The oxidative stress is caused by strong oxidizing ability possessed by excessive reactive oxygen species or free radicals in cells. Most of superoxide anion radicals ($O_2^-$.) are generated by an electron leakage in the process from the Krebs cycle to the electron transport system in mitochondria. Moreover, $O_2^-$. is also generated by oxidase such as NADPH oxidase or xanthine oxidase. $O_2^-$. is converted to hydrogen peroxide by superoxide dismutase. This hydrogen peroxide is further converted for detoxication to water by glutathione peroxidase or catalase. Excessive $O_2^-$. reduces iron or copper, which is a transition metal. These reduction products react with hydrogen peroxide through the Fenton reaction to generate hydroxyl radicals (.OH). .OH, which is the strongest reactive oxygen species, indiscriminately reacts with nucleic acids, lipids, and proteins. A mechanism for detoxicating this .OH is unknown. Thus, the removal of .OH is the most important antioxidation process.

Protection from the poisonous influence of free radical molecules is found in molecules called antioxidants from diverse regions. In vivo free radical molecules and their related by-products may be converted to less harmful products by neutralization brought by antioxidants. Such antioxidants can be enzymes (superoxide dismutase, catalase, glutathione peroxidase, etc.), essential nutrients (beta-carotene, vitamin C and E, selenium, etc.), enormous numbers of endogenous substances (glutathione etc.), or food compounds (bioflavonoid etc.). Thus, humans have some natural inhibitors against free radical molecules in their bodies.

However, individuals suffer a great deal of damage by free radical molecules, in spite of the presence of such in vivo free radical inhibitors. Thus, it is obvious that effects including nutritional supplementation for the prevention of oxidation induced by free radical molecules delay human aging process and have big advantages to health promotion and the prevention of disease.

Meanwhile, the oxidation-reduction potential of hydrogen molecules is −0.42 V, and the oxidation-reduction potential of oxygen molecules is +0.82 V. Thus, hydrogen molecules have the intrinsic ability to reduce oxygen molecules. However, the oxidation-reduction potentials are indicators for oxidizing or reducing ability and merely indicate the final stage of oxidation-reduction reactions in an equilibrium state. Whether or not oxidation-reduction reactions actually proceed in vivo is another story. In general, the rapid progress of reactions requires catalysts or the like or requires promoting reactions at a high temperature. In cells having complex structures, the progress of oxidation-reduction reactions often requires their respective specific enzymes. Thus, it is impossible to predict whether hydrogen actually exhibits reducing power in vivo.

For example, according to the oxidation-reduction potentials, hydrogen and oxygen should be converted to water through a reaction. However, hydrogen and oxygen molecules dissolved in water are not converted to water through a reaction. Likewise, whether hydrogen molecules can reduce reactive oxygen species or free radicals, as described above, can be confirmed only by actual experiments. Judging from the oxidation-reduction potentials, hydrogen molecules are supposed to reduce superoxide, nitrogen monoxide, and hydrogen peroxide in an equilibrium state. Meanwhile, superoxide, hydrogen peroxide, and nitrogen monoxide have been demonstrated to play roles indispensable to living bodies. These roles are killing effects on invading bacteria, immune functions, defensive mechanisms against cancers, vascularization, vasodilation, spermatogenesis, neurotransmission, and so on. Thus, if hydrogen molecules rapidly eliminate these free radicals or reactive oxygen species in vivo through reduction, the hydrogen molecules should sometimes be harmful.

Water with a low oxidation-reduction potential has heretofore been prepared by electrolysis (see Patent Documents 1 to 3 below) or by dissolving hydrogen under pressure (see Patent Document 4 below). Of them, an aqueous drink with a low oxidation-reduction potential prepared by an electrolysis method merely exhibits alkaline properties attributed to OH⁻ ions and does not contain hydrogen gas at a saturated concentration or higher. Such an alkaline aqueous drink has reducing power attributed to the OH⁻ ions and therefore apparently exhibits reducing properties. However, this aqueous drink results in a high oxidation-reduction potential, when rendered neutral. This means that it exhibits apparent reducing properties. Moreover, the drinking of alkaline solutions in large amounts presents a health problem. Particularly, such alkaline solutions put a severe strain on the kidney and are therefore harmful to persons with renal damage. On the other hand, the alkaline solutions, if in appropriate amounts, are observed to have a few effects on persons with gastric hyperacidity. However, these effects are merely effects brought by the neutralization of gastric acid by the alkaline solutions and are not the effects of hydrogen gas or reducing power.

Moreover, another known method comprises mixing metal magnesium into an aqueous drink to thereby obtain reductive water. In this case, magnesium and OH⁻ ions are generated simultaneously with hydrogen gas. Therefore, this reductive water is alkaline. Magnesium ions, if in appropriate amounts, can be expected to have health maintenance effects on human bodies, because they have been applied to laxatives and the like. However, the ingestion of such alkaline aqueous drinks in large amounts, as already described, works to inhibit the body function of being constantly neutral and is therefore dangerous. Rather, a drink prepared by simply dissolving hydrogen gas does not exhibit alkaline properties and therefore probably has higher safety.

Patent Document 1: JP Patent Publication (Kokai) No. 2001-145880A (2001)
Patent Document 2: JP Patent Publication (Kokai) No. 2001-137852A (2001)
Patent Document 3: JP Patent Publication (Kokai) No. 2002-254078A (2002)
Patent Document 4: JP Patent Publication (Kokai) No. 2004-230370A (2004)

DISCLOSURE OF THE INVENTION

Free radical molecules, as described above, have been known to have strong oxidizing power and place oxidative stress on living bodies. It has heretofore been suggested that polyphenols, vitamins, and the like are effective for the prevention of oxidative stress. Each of vitamin C and E, which have been accepted and ingested most widely for the prevention of this oxidative stress, is highly safe and inexpensive. However, vitamin C is soluble in water, whereas vitamin E is soluble in fat. Therefore, both of these vitamins cannot easily reach the internal regions of cells. Thus, antioxidants that are capable of widely penetrating into the internal and external regions of cells have been demanded.

Meanwhile, not only are free radicals harmful, but also they have been demonstrated to play roles indispensable to living bodies. These roles are killing effects on invading bacteria, immune functions, defensive mechanisms against cancer, vascularization, vasodilation, spermatogenesis, neurotransmission, and so on. These roles are brought by superoxide, hydrogen peroxide, and nitrogen monoxide. Thus, if a substance capable of selectively removing only highly reactive and highly cytotoxic free radical species such as hydroxyl radicals, peroxynitrite, and lipid peroxyl radicals can be found, such a substance can be used safely in defense against oxidative stress and is therefore desirable.

Antioxidants including antioxidative vitamin, as described above, have heretofore been utilized in health promotion as agents for eliminating free radicals or reactive oxygen species. However, these agents cannot always easily reach the internal regions of cells. Alternatively, even if the reductive water as disclosed in Patent Documents 1 to 4 above is drank, it is obvious that this reductive water is not capable of widely penetrating into the internal and external regions of cells, with its reducing properties maintained. In addition, the structures and components of living bodies are complicated and are not homogeneous systems. Therefore, the effects of the reductive water cannot easily be predicted.

The present inventors have considered that hydrogen molecules in a gas state are taken up into living bodies and rapidly distributed into cells, and such hydrogen molecules can be expected to eliminate free radicals at a point in time when the free radicals are generated. Thus, the present inventors have conducted various studies and have consequently completed the present invention by confirming that hydrogen molecules can alleviate damage caused by free radicals in cells; hydrogen molecules are actually taken up into the bodies of animals including humans; and hydrogen actually alleviates oxidative stress in the bodies of animals.

Specifically, an object of the present invention is to provide a scavenger of free radicals, which is capable of effectively reducing the concentrations of in vivo free radicals and exhibiting given effects such as the suppression of aging process, the prevention of geriatric or lifestyle-related diseases, health promotion, and the inhibition of oxidative stress by virtue of this reduction in the concentrations of free radicals, and to provide an apparatus for the inhalation of this scavenger of free radicals.

$O_2^-$. or hydrogen peroxide with a low concentration functions as a signal molecule for controlling a large number of signal transduction cascades, in spite of its cytotoxicity, and has physiologically important functions such as the control of physiological processes, for example, apoptosis, cell growth, and cell differentiation. Hydrogen peroxide with a high concentration is converted to hypochlorous acid by myeloperoxidase, and this hypochlorous acid exhibits antimicrobial effects. Furthermore, nitrogen monoxide radicals, which are neurotransmitters, play an important role in vasodilation. By contrast, radicals having unilateral cytotoxicity, such as .OH, can be neutralized by hydrogen molecules without inhibiting basic physiological activities possessed by reactive oxygen species as described above. The present inventors have completed the present invention by finding that hydrogen molecules can alleviate .OH-induced cytotoxicity without influencing other reactive oxygen species, and hydrogen molecules have the potential of being applicable as an antioxidant to medical care.

Specifically, the present invention is as follows:

[1] A scavenger of in vivo harmful reactive oxygen species and/or free radicals comprising a liquid comprising at least a hydrogen molecule.

[2] The scavenger of in vivo harmful reactive oxygen species and/or free radicals according to [1], wherein the liquid comprising at least a hydrogen molecule comprises an aqueous solution.

[3] The scavenger of in vivo harmful reactive oxygen species and/or free radicals according to [2], wherein the hydrogen molecule comprised therein is supersaturated.

[4] The scavenger of in vivo harmful reactive oxygen species and/or free radicals according to [2] or [3], further comprising an oxygen molecule.

[5] The scavenger of in vivo harmful reactive oxygen species and/or free radicals comprising a gas comprising at least a hydrogen molecule.

[6] The scavenger of in vivo harmful reactive oxygen species and/or free radicals according to [5], wherein the gas comprising at least a hydrogen molecule comprises a mixed gas of hydrogen and oxygen gases.

[7] The scavenger of in vivo harmful reactive oxygen species and/or free radicals according to [5], wherein the gas comprising at least a hydrogen molecule comprises a mixed gas of hydrogen, oxygen, and inactive gases.

[8] The scavenger of in vivo harmful reactive oxygen species and/or free radicals according to [5], wherein the gas comprising at least a hydrogen molecule comprises a mixed gas of a hydrogen gas and air.

[9] The scavenger of in vivo harmful reactive oxygen species and/or free radicals according to [5], wherein the gas comprising at least a hydrogen molecule comprises a mixed gas of hydrogen and anesthetic gases.

[10] The scavenger of in vivo harmful reactive oxygen species and/or free radicals according to any of [5] to [9], wherein the removing agent comprises the hydrogen gas at a concentration of 1 to 4% (v/v).

[11] The scavenger of in vivo harmful reactive oxygen species and/or free radicals according to any of [5] to [9], wherein the removing agent comprises the hydrogen gas at a concentration of 1.5 to 2.5% (v/v).

[12] The scavenger of in vivo harmful reactive oxygen species and/or free radicals according to any of [1] to [11], wherein the active oxygen and/or free radicals are active oxygen and/or free radicals selected from the group consisting of hydroxyl radicals, peroxynitrite, alkoxy radicals, and lipid peroxyl radicals.

[13] The scavenger of in vivo harmful reactive oxygen species and/or free radicals according to [12], wherein the active oxygen and/or free radicals are hydroxyl radicals.

[14] A pharmaceutical composition comprising the scavenger of in vivo harmful reactive oxygen species and/or free radicals according to any of [1] to [13].

[15] A therapeutic or preventive agent for a disorder attributed to reactive oxygen species and/or free radicals, the therapeutic or preventive agent comprising the scavenger of in vivo harmful reactive oxygen species and/or free radicals according to any of [1] to [13].

[16] The therapeutic or preventive agent according to [15], wherein the disorder attributed to reactive oxygen species and/or free radicals is selected from the group consisting of oxidative stress, oxidative stress-induced cell death, and oxidative stress-induced mitochondrial dysfunction.

[17] The therapeutic or preventive agent according to [15], wherein the disorder attributed to reactive oxygen species and/or free radicals is selected from the group consisting of cerebral infarction, myocardial infarction, arteriosclerosis, ischemia-reperfusion injury, disorders caused by organ transplantation, retinal degeneration in premature babies, acute pneumonopathy, disorders caused by artificial dialysis, inflammation, and disturbance of lipid metabolism.

[18] The therapeutic or preventive agent according to [15], wherein the disorder attributed to reactive oxygen species and/or free radicals is myopathy after strenuous exercise or oxygen injury caused by oxygen gas inhalation at a high concentration after exercise.

[19] The therapeutic or preventive agent according to [15], wherein the disorder attributed to reactive oxygen species and/or free radicals is selected from the group consisting of neurodegenerative diseases including Alzheimer's disease, Parkinson's disease, and ALS.

[20] The therapeutic or preventive agent according to [15], wherein the disorder attributed to reactive oxygen species and/or free radicals is cancer.

[21] A drink suitable for the alleviation or prevention of a disorder attributed to reactive oxygen species and/or free radicals, the drink comprising the scavenger of reactive oxygen species and/or free radicals comprising a liquid comprising at least a hydrogen molecule according to any of [1] to [4].

[22] A drink with a label stating that the drink is used for the scavenging or reduction of in vivo reactive oxygen species and/or free radicals, the drink comprising the scavenger of reactive oxygen species and/or free radicals comprising a liquid comprising at least a hydrogen molecule according to any of [1] to [4].

[23] A drink with a label stating that the drink is used for the alleviation or prevention of a disorder attributed to reactive oxygen species and/or free radicals, the drink comprising the scavenger of reactive oxygen species and/or free radicals comprising a liquid comprising at least a hydrogen molecule according to any of [1] to [4].

[24] The drink according to any of [21] to [23], wherein the drink is a health food, functional food, nutritional supplementary food, supplement, or food for specified health use.

[25] A container comprising the scavenger of in vivo harmful reactive oxygen species and/or free radicals according to any of [5] to [10].

[26] The container according to [25], wherein the container is a hydrogen gas cylinder.

[27] An apparatus for supplying a scavenger of reactive oxygen species and/or free radicals to a subject in need of the treatment or prevention of a disorder attributed to reactive oxygen species and/or free radicals, the apparatus comprising: a container comprising the scavenger of in vivo harmful reactive oxygen species and/or free radicals comprising a gas comprising at least a hydrogen molecule according to any of [5] to [10]; gas inhalation means; and a supply duct for supplying a gas in the container to the inhalation means.

[28] The apparatus for supplying the scavenger of reactive oxygen species and/or free radicals to a subject in need of the treatment or prevention of a disorder attributed to reactive oxygen species and/or free radicals according to [27], the apparatus further comprising a container comprising at least one gas selected from the group consisting of oxygen gas, inactive gases, and air, wherein the scavenger of in vivo harmful reactive oxygen species and/or free radicals comprising a gas comprising at least a hydrogen molecule, and the at least one gas selected from the group consisting of oxygen gas, inactive gases, and air are supplied separately or as a mixture to the gas inhalation means.

[29] The apparatus for supplying the scavenger of reactive oxygen species and/or free radicals to a subject in need of the treatment or prevention of a disorder attributed to reactive oxygen species and/or free radicals according to [27] or [28], the apparatus further comprising a container comprising an anesthetic gas, wherein the scavenger of in vivo harmful reactive oxygen species and/or free radicals comprising a gas comprising at least a hydrogen molecule, and the anesthetic gas are supplied separately or as a mixture to the gas inhalation means.

[30] The apparatus for supplying the scavenger of reactive oxygen species and/or free radicals to a subject in need of the treatment or prevention of a disorder attributed to reactive oxygen species and/or free radicals according to any of [27] to [29], wherein the container comprising the scavenger of in vivo harmful reactive oxygen species and/or free radicals comprising a gas comprising at least a hydrogen molecule comprises 1 to 4% hydrogen gas.

[31] The apparatus for supplying the scavenger of reactive oxygen species and/or free radicals to a subject in need of the treatment or prevention of a disorder attributed to reactive oxygen species and/or free radicals according to any of [27] to [30], wherein the container comprising the scavenger of in vivo harmful reactive oxygen species and/or free radicals comprising a gas comprising at least a hydrogen molecule is a hydrogen gas cylinder.

[32] The apparatus for supplying the scavenger of reactive oxygen species and/or free radicals to a subject in need of the treatment or prevention of a disorder attributed to reactive oxygen species and/or free radicals according to any of [27] to [31], wherein the gas inhalation means is a gas inhalation mask.

[33] The apparatus for supplying the scavenger of reactive oxygen species and/or free radicals to a subject in need of the treatment or prevention of a disorder attributed to reactive oxygen species and/or free radicals according to any of [27] to [31], wherein the gas inhalation means is a sealed chamber, and the scavenger of in vivo harmful reactive oxygen species and/or free radicals comprising a gas comprising at least a hydrogen molecule is supplied into the sealed chamber to thereby supply the scavenger of reactive oxygen species and/or free radicals to the subject in the sealed chamber.

The present specification encompasses the contents described in the specifications and/or drawings of Japanese Patent Application Nos. 2005-2385725 and 2006-157827 that serve as a basis for the priority of the present application.

BRIEF DESCRIPTION OF THE DRAWINGS

FIG. 40 is a diagram showing the number of GST-P-positive cell foci in the livers of hydrogen water-administered or hydrogen water-unadministered mice (FIG. 40a) and the areas of the positive foci (FIG. 40b).

BEST MODE FOR CARRYING OUT THE INVENTION

Figure 1:
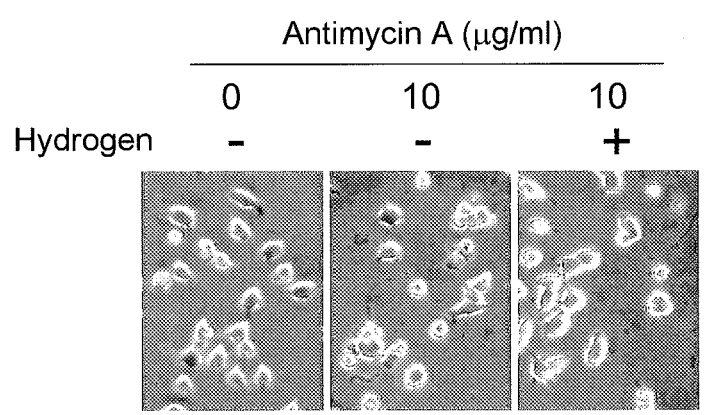
FIG. 1 is a phase contrast microscopic image of antimycin A-treated PC 12 cells in a hydrogen-containing medium.

Hydrogen can remove in vivo reactive oxygen species and/or free radicals through reduction in a living body.

Reactive oxygen species refer to molecules that have the high ability to oxidize other substances by stronger oxidizing power than that of oxygen and refer to singlet oxygen, hydrogen peroxide, ozone, superoxide radicals, hydroxyl radicals, peroxynitrite, and the like. Free radicals encompass nitrogen monoxide, alkoxyl radicals (lipid radicals; L.), lipid peroxyl radicals (alkylperoxyl radicals; LOO.), and the like, in addition to the reactive oxygen species such as superoxide or hydroxyl radicals. In the present invention, the free radicals also mean, in the broad sense, free radical molecules including reactive oxygen species.

Of them, hydroxyl radicals, peroxynitrite, alkoxy radicals, and lipid peroxyl radicals are bad reactive oxygen species or free radicals with cytotoxicity that have harmful effects on living bodies and can be one of causes of various disorders. In the present invention, hydrogen exclusively removes these harmful reactive oxygen species and/or free radicals in a short time through reduction. On the other hand, reactive oxygen species and/or free radicals other than the bad reactive oxygen species and/or free radicals participate in signal transduction and so on in vivo and have useful functions. Such reactive oxygen species and/or free radicals are referred to as good reactive oxygen species and/or free radicals. The good reactive oxygen species and/or free radicals are not easily removed by even hydrogen. A scavenger of in vivo harmful reactive oxygen species and/or free radicals comprising a liquid comprising at least a hydrogen molecule according to the present invention exclusively removes only bad reactive oxygen species and/or free radicals harmful to living bodies. In this context, oxidative stress refers to a disorder in living bodies brought by the oxidizing power of reactive oxygen species and/or free radicals.

Hydrogen molecules are capable of passing through even cell membranes. Therefore, they enter into cells and remove reactive oxygen species and/or free radicals in the cells. Moreover, the hydrogen molecules can also enter into nuclei and mitochondria. Thus, they can protect genes from reactive oxygen species and/or free radicals and can inhibit cancer. Moreover, hydrogen is capable of passing through the blood-brain barrier and can therefore protect the brain from oxidative stress.

The liquid comprising at least a hydrogen molecule is characterized by comprising an aqueous solution. Pure water, ion-exchanged water, distilled water, a saline, and the like may be used as a medium forming this aqueous solution. Furthermore, the scavenger of in vivo harmful free radicals obtained by using pure water, ion-exchanged water, or distilled water as the medium may be added for drinking to general aqueous drinks, for example, mineral water, juice, coffee, and tea. In this context, the drink encompasses health foods, foods for specified health use, foods with nutrient function claims, nutritional supplementary foods, supplements, and the like for drinking. In this context, the foods for specified health use refer to foods with a label stating that the food can be ingested for specified health purposes in diets and expected to satisfy the health purposes by this ingestion. These drinks may be provided with a label stating that the drink is used for the removal or reduction of in vivo reactive oxygen species and/or free radicals or a label stating that the drink is used for the alleviation or prevention of a disorder attributed to free radicals. Furthermore, the drinks may be provided with a label specifically defining disorders attributed to reactive oxygen species and/or free radicals and stating that the drink is used for the alleviation or prevention of the defined disorders or may be provided with a label stating that the drink is useful for antiaging or antioxidation. Furthermore, the liquid comprising hydrogen may be used in cosmetics for similar purposes.

The hydrogen molecule, which may be supersaturated, can be dissolved in water or an aqueous solution for a certain period. The water or aqueous solution comprising such a supersaturated hydrogen molecule can be produced by dissolving hydrogen gas in water or an aqueous solution under pressure and then removing the pressure. For example, the aqueous solution may be placed under hydrogen gas pressure of 0.4 MPa or higher for a few hours, preferably, 1 to 3 hours. The scavenger of in vivo harmful reactive oxygen species and/or free radicals in an aqueous solution form can also be used for drinking or can also be used for intravenous injection in the form of a saline comprising oxygen coexisting therewith. In this case, administration may be administration using catheters or administration using injection. After administration, the hydrogen ingested into living bodies is mostly absorbed into the living bodies and distributed into the whole bodies via blood. The distributed hydrogen exhibits its effects therein and is then excreted together with breath.

Hydrogen can be dissolved in an amount of approximately 17.5 mL per L of water (approximately 1.6 ppm, approximately 0.8 mM) under conditions involving a hydrogen pressure of 1 atm and room temperature. The scavenger of reactive oxygen species and/or free radicals in an aqueous solution form according to the present invention comprises 10 mL or higher, preferably 15 mL or higher, particularly preferably 17.5 mL or higher of hydrogen molecule per L of aqueous solution. Alternatively, the scavenger of reactive oxygen species and/or free radicals in an aqueous solution form according to the present invention comprises 1 ppm or higher, preferably 1.5 ppm or higher hydrogen molecule. Alternatively, the scavenger of reactive oxygen species and/or free radicals in an aqueous solution form according to the present invention comprises 0.1 mM or higher, preferably 0.4 mM or higher, more preferably 0.6 mM, particularly preferably 0.8 mM or higher hydrogen.

Moreover, the scavenger of reactive oxygen species and/or free radicals in an aqueous solution form according to the present invention may comprise an oxygen molecule. The hydrogen and oxygen molecules coexist in the aqueous solution. However, the hydrogen and oxygen molecules do not immediately react with each other even in a mixed state and can coexist stably. However, when gases contain a large amount of oxygen molecules, it is preferred for securing safety that a hydrogen content should be set to less than 4.7% (v/v) of the total gas amount. In a use environment with no safety problem, it is preferred that a hydrogen content should be as high a concentration as possible. The scavenger of reactive oxygen species and/or free radicals comprising oxygen may also be used for drinking or for intravenous injection in the form of a saline. In administration using injection, such a scavenger comprising oxygen causes less damage to tissues in living bodies than that caused by an oxygen molecule-free scavenger, because the living bodies are not placed under local oxygen-deficient conditions.

For a drink of the present invention, it is preferred that the drink should be stored in a container made of a raw material impermeable to hydrogen, preferably, aluminum or the like. Examples of such a container include aluminum pouches. Moreover, it is preferred that the drink should be stored at a low temperature, because a larger amount of hydrogen is dissolved at a lower temperature.

The scavenger of in vivo harmful reactive oxygen species and/or free radicals comprising at least a hydrogen molecule according to the present invention may be in a gas form. In this case, a hydrogen concentration is 1 to 4.7%, preferably 1 to 4.5%, more preferably 1 to 4% (v/v), even more preferably 1.5 to 2.5% (v/v), still even more preferably approximately 2%. It is desired for securing safety that a hydrogen gas content should be less than approximately 4.7% (v/v). However, the hydrogen gas content can also be increased more under safe conditions that make consideration to generate no static electricity under sealed conditions. The scavenger of in vivo harmful reactive oxygen species and/or free radicals comprising at least a hydrogen molecule according to the present invention may further comprise an oxygen gas and/or other inactive gases. Such a removing agent comprising an oxygen gas comprises a mixed gas of hydrogen and oxygen gases. The oxygen gas is consumed for respiration. A nitrogen gas, helium gas, argon gas, or the like may be used as the inactive gas. An inexpensive nitrogen gas is desirable. The content of this inactive gas can be set arbitrarily by those skilled in the art so as not to be too large. In consideration of an oxygen gas concentration for respiration, it is preferred that the inactive gas content should be 80% (v/v) or lower. Furthermore, the scavenger of in vivo harmful reactive oxygen species and/or free radicals comprising at least a hydrogen molecule according to the present invention may be a mixed gas of a hydrogen gas and air. Such a mixed gas can be produced easily by appropriately mixing hydrogen gas with air. Furthermore, the scavenger of in vivo harmful reactive oxygen species and/or free radicals comprising a hydrogen molecule according to the present invention may comprise an anesthetic gas. In this case, the scavenger of in vivo harmful reactive oxygen species and/or free radicals comprises a mixed gas of hydrogen and anesthetic gases. Examples of the anesthetic gas include nitrous oxide.

The scavenger of in vivo harmful reactive oxygen species and/or free radicals in a gas form comprising at least a hydrogen molecule according to the present invention is placed in a pressure-resistant container, for example, a gas cylinder. The present invention encompasses even a container comprising the scavenger of in vivo harmful reactive oxygen species and/or free radicals in a gas form comprising at least a hydrogen molecule.

The scavenger of in vivo harmful reactive oxygen species and/or free radicals in a gas form comprising at least a hydrogen molecule according to the present invention can be inhaled by a subject. The inhalation can be performed using inhalation means. The scavenger of in vivo harmful reactive oxygen species and/or free radicals may be inhaled via the inhalation means through a duct from the container comprising the scavenger. The inhalation means is not limited. Examples thereof include inhalation masks. The mask, preferably, can cover both the mouth and nose of a subject. Furthermore, the inhalation means may be a small sealed chamber that is hermetically sealed. The small chamber has a size that is large enough to accommodate a subject therein. The scavenger of in vivo harmful reactive oxygen species and/or free radicals in a gas form comprising at least a hydrogen molecule according to the present invention can be supplied to the small chamber accommodating a subject therein and thereby inhaled by the subject. One example of such a small chamber includes enclosed beds. A subject lying in the bed can inhale the scavenger of in vivo harmful reactive oxygen species and/or free radicals in a gas form comprising at least a hydrogen molecule according to the present invention.

The present invention also encompasses a composition such as a pharmaceutical composition comprising, as an active ingredient, a scavenger of in vivo harmful reactive oxygen species and/or free radicals comprising a liquid comprising at least a hydrogen molecule. In this case, the scavenger of reactive oxygen species and/or free radicals may be in a liquid form or in a gas form. Such a composition can be used for the prevention or treatment of a disorder attributed to reactive oxygen species and/or free radicals.

In this context, the disorder attributed to reactive oxygen species and/or free radicals refers to a disorder, disease, dysfunction, or the like, one of causes of which is reactive oxygen species and/or free radicals. Specific examples thereof include oxidative stress, oxidative stress-induced cell death, and oxidative stress-induced mitochondrial dysfunction. Alternative examples thereof include cerebral infarction, myocardial infarction, ischemia-reperfusion injury caused by operation or the like, disorders caused by organ transplantation, retinal degeneration in premature babies, acute pneumonopathy, disorders caused by artificial dialysis, and inflammation. Further examples thereof include myopathy after strenuous exercise and oxygen injury caused by oxygen gas inhalation at a high concentration after exercise. Further examples thereof include neurodegenerative diseases such as Alzheimer's disease, Parkinson's disease, and ALS. Furthermore, the scavenger of reactive oxygen species and/or free radicals of the present invention can also be used in the prevention or treatment of cancer by preventing nuclear DNA oxidation. Furthermore, reactive oxygen species and/or free radicals participate in aging process. The scavenger of reactive oxygen species and/or free radicals of the present invention is capable of exhibiting antiaging effects by the treatment or prevention of various disorders associated with aging. Specifically, the scavenger of reactive oxygen species and/or free radicals of the present invention can also be used as a composition useful for antiaging. Of these disorders, cerebral infarction and myocardial infarction are caused by reactive oxygen species and/or free radicals occurring due to blood flow under oxygen-deficient conditions. Alternatively, ischemia-reperfusion injury caused by operation is caused by reactive oxygen species and/or free radicals occurring due to blood flow that is stopped during operation and restarted at the completion of operation. Moreover, in organ transplantation, an organ to be transplanted is placed under oxygen-deficient conditions, and disorders are caused by reactive oxygen species and/or free radicals occurring due to blood flow after transplantation. Retinal degeneration in premature babies is a disorder in the retina of premature babies that is caused by reactive oxygen species easily occurring due to high-concentration oxygen therapy for the premature babies. Acute pneumonopathy is caused by reactive oxygen species and/or free radicals occurring due to high-concentration oxygen therapy. Furthermore, immediately after strenuous exercise, disorders are caused by reactive oxygen species and/or free radicals occurring due to oxygen supply by the termination of the exercise after oxygen-deficient conditions.

In the present invention, prevention or treatment encompasses the curing of a disorder by the administration of the scavenger of reactive oxygen species and/or free radicals to a subject actually having the disorder, the reduction of risk of a disorder by the administration of the scavenger of reactive oxygen species and/or free radicals to a subject at risk of the disorder, the alleviation of the degree of the disorder, and the suppression of the disorder.

The timing of administration or ingestion of these compositions is not limited. The compositions may be administered or ingested, when the disorder actually occurs. Alternatively, the compositions may be administered or ingested immediately before or after the in vivo occurrence of reactive oxygen species and/or free radicals. For example, it is preferred that the administration or ingestion should be performed after strenuous exercise, in oxygen ingestion after strenuous exercise, after the occurrence of mental stress or physical stress, and so on. Furthermore, cigarette smoke contains a large amount of superoxide radicals, which are in turn converted to hydroxyl radicals in vivo. Gene damage caused by these hydroxyl radicals is allegedly one of causes of lung cancer. Thus, the scavenger of reactive oxygen species and/or free radicals of the present invention can be used in the prevention of lung cancer in smokers.

The scavenger of reactive oxygen species and/or free radicals in a liquid form can be administered by oral administration or intravenous injection. Alternatively, for local disease such as cancer, the scavenger of reactive oxygen species and/or free radicals in a liquid form may be administered directly to the cancer site. For example, to visceral cancer, the scavenger of reactive oxygen species and/or free radicals in a liquid form may be administered by intraperitoneal injection. Alternatively, the scavenger of reactive oxygen species and/or free radicals in a gas form may be administered by inhalation.

Figure 36:
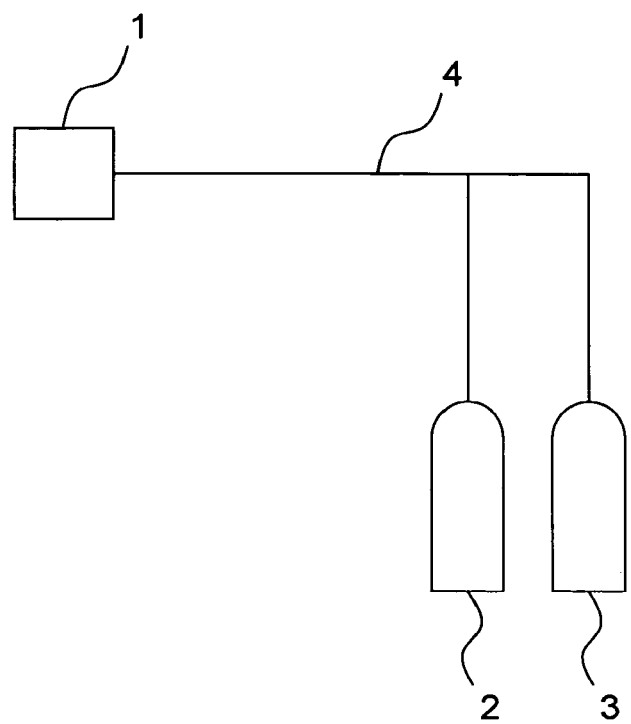
FIG. 36 is a diagram showing an apparatus of the present invention.

The present invention further encompasses an apparatus for supplying a scavenger of reactive oxygen species and/or free radicals to a subject in need of the treatment or prevention of a disorder attributed to reactive oxygen species and/or free radicals, the apparatus comprising: a container comprising a scavenger of in vivo harmful reactive oxygen species and/or free radicals comprising a gas comprising at least a hydrogen molecule; gas inhalation means; and a supply duct for supplying a gas in the container to the inhalation means. The container is, for example, a hydrogen gas cylinder. Moreover, examples of the gas inhalation means include inhalation masks and sealed small chambers, as described above. The apparatus may further comprise a container comprising at least one gas selected from the group consisting of oxygen gas, inactive gases, air, and anesthetic gases. In this case, the scavenger of in vivo harmful reactive oxygen species and/or free radicals comprising a gas comprising at least a hydrogen molecule, and the at least one gas selected from the group consisting of oxygen gas, inactive gases, and air may be supplied separately or as a mixture to the gas inhalation means. FIG. 36 shows a schematic diagram of the apparatus of the present invention. In the diagram, the apparatus comprises gas inhalation means 1, a container 2 comprising a scavenger of in vivo harmful reactive oxygen species and/or free radicals comprising a gas comprising a hydrogen molecule, a container 3 comprising at least one gas selected from the group consisting of oxygen gas, inactive gases, air, and anesthetic gases, and a duct 4. The gas is supplied to the gas inhalation means through the duct and administered to the subject.

Hereinafter, specific embodiments of the present invention will be described in detail with reference to Examples. However, the present invention is not intended to be limited to these Examples below. The present invention can also be applied to various changes or modifications without departing from technical principles shown in claims.

In Examples below, hydrogen and oxygen measurements, the hydrogen treatment of cultured cells, and the staining of cultured cells are performed by approaches shown below, unless otherwise specified. Moreover, detailed conditions are shown in each Example.

Hydrogen and Oxygen Measurements

Hydrogen and oxygen concentrations in solutions were measured with a hydrogen electrode (ABLE & Biott Co., Ltd.) and an oxygen electrode (Strathkelvin Instruments Ltd.), respectively. A hydrogen gas concentration was measured by gas chromatography (TERAMECS CO., LTD., Kyoto, Japan). RF-5300PC (manufactured by Shimadzu Corp.) was used in fluorescence intensity measurement. In experiments under solution conditions, solutions were left at a hydrogen gas pressure of 0.4 MPa for 2 hours to thereby dissolve hydrogen therein. In measurement experiments on the elimination of hydroxyl radicals by hydrogen, a phosphate buffer (10 mM, pH 7.4), ferrous hydroxide (0.1 mM), and HPF (0.4 µM; Daiichi Pure Chemicals Co., Ltd.) were added to the solution containing dissolved hydrogen, and a concentration was measured with a hydrogen electrode. Subsequently, hydrogen peroxide (5 µM) was added thereto to initiate the Fenton reaction, and the mixture was gently stirred at 23° C.

Hydrogen Treatment of Cultured Cells

A DMEM medium was left at a hydrogen gas pressure of 0.4 MPa for 2 hours to thereby dissolve hydrogen therein. An oxygen-saturated medium was additionally prepared by aerating a medium with oxygen gas and mixed with the medium containing dissolved hydrogen to bring a dissolved oxygen concentration at 25° C. to 8.5 mg/L. Moreover, a hydrogen concentration was measured with a hydrogen electrode. To generate .OH via $O_2^-$., antimycin A was added to cells. PC12 cells were placed in a sealed container that enclosed gases containing hydrogen and oxygen at appropriately adjusted concentrations of dissolved hydrogen and dissolved oxygen. The cells were cultured at 37° C.

Staining of Cultured Cells

In .OH detection, HPF (0.4 µM) was added to a cell medium, and the fluorescence image thereof was observed using a confocal laser scanning microscope (FV300 manufactured by Olympus Corp.) at an excitation wavelength of 488 nm and an absorption wavelength of 510 nm. MitoTracker Green (1 µM; Molecular Probes) and MitoTracker Red (100 nM; Molecular Probes) were used in the staining of mitochondria. Anti-HNE and anti-8-OH-G antibodies were purchased from Nikken Seil Co., Ltd. Moreover, anti-TUJ-1 and anti-GFAP antibodies were purchased from Babco and Immunon, respectively.

Example 1

Hydrogen molecules have been known to have reducing power. However, it is impossible to predict, as described above, whether hydrogen molecules can reduce, in a short time, molecular species participating in biologically important oxidation-reduction, and free radical molecules. Thus, in Example 1, hydrogen water was used to measure effects on each molecular species.

Preparation of Hydrogen Water

First, 1 l of water was injected into a 5-l pressure-resistant bottle (manufactured by UNICONTROLS. CO., LTD.). Then, hydrogen gas was charged thereinto at a pressure of 0.4 MPa. After 2 hours, water supplemented with hydrogen was collected from the bottle under reduced pressure. A hydrogen content was analyzed using a dissolved hydrogen measuring apparatus (manufactured by ABLE & Biott Co., Ltd.). Water containing approximately 0.8 mM saturated hydrogen (hydrogen water) was obtained by this method.

Measurement of Reactive Oxygen Species Eliminating Effects of Hydrogen Water

Subsequently, for nitrogen monoxide NO, 0.1 mM or 1 mM 1-Hydroxy-2-oxo-3-(N-methyl-3-aminopropyl)-3-methyl-1-triazene (NOC7; manufactured by DOJINDO Co.) serving as an NO donor was added to the hydrogen water adjusted to pH 7.4 with 0.01 M phosphate. After reaction at room temperature for 30 minutes, 1 µM 5-(and -6)-chloromethyl-2',7'-dichlorodihydrofluorescein diacetate (DCFDH; manufactured by Molecular Probe, USA) was subsequently added thereto. The amount of NO remaining was measured with a fluorescence analyzer (manufactured by TECAN, Austria) at an excitation wavelength of 485 nm.

For peroxynitrite (ONOO$^-$), a peroxynitrite solution (manufactured by DOJINDO Co.) was added at a final concentration of 62.3 mM to the hydrogen water adjusted to pH 7.4 with 0.01 M phosphate. After reaction at room temperature for 10 minutes, absorbance at 300 nm was subsequently measured using a spectrophotometer (manufactured by BECKMAN).

For hydrogen peroxide $H_2O_2$, hydrogen peroxide water (manufactured by Wako Pure Chemical Industries, Ltd.) was added at a final concentration of 100 µM to 1 µM to the hydrogen water. After reaction at room temperature for 30 minutes, 0.2 M phosphate buffer (pH 7.2) containing an equal amount of 20 µM DCFDA was subsequently added thereto. After reaction for 10 minutes, the amount of $H_2O_2$ remaining was measured with a fluorescence analyzer at an excitation wavelength of 485 nm.

For hydroxyl radicals (.OH), ferrous perchlorate (manufactured by Aldrich) at a final concentration of 100 µM, 1 mM hydrogen peroxide, and 1 pM 2-[6-(4'-hydroxy)phenoxy-3H-xanthen-3-on-9-yl]benzoic acid (HPF; manufactured by DOJINDO Co.) were added to the hydrogen water. After reaction for 10 minutes, the amount of .OH remaining was measured with a fluorescence analyzer at an excitation wavelength of 485 nm. HPF is less reactive with hydrogen peroxide and highly reactive with hydroxyl radicals to emit fluorescence. As a result, the amount of hydroxyl radicals remaining was measured.

0.1 mM 2,2'-azobis(2-amidinopropane) dihydrochloride (manufactured by Wako Pure Chemical Industries, Ltd.) that generates lipid peroxyl radicals (alkylperoxyl radicals) (LOO.) as an indicator for lipid radicals was added to the hydrogen water. After reaction at room temperature for 1 hour, 0.2 M phosphate buffer (pH 7.2) containing an equal amount of 20 µM DCFDA was subsequently added thereto. After reaction for 10 minutes, the amount of LOO. remaining was measured with a fluorescence analyzer at an excitation wavelength of 485 nm.

For superoxide ($O_2^-$.), 25× Reaction Buffer, Xanthine Solution, and NBT Solution contained in TREVIGEN Superoxide Dismutase Assay Kit were mixed with the hydrogen water according to the manufacturer's manual. Then, a Xanthine oxidase solution was added thereto to thereby generate $O_2^-$.. NBT-diformazan accumulation was measured over time with a spectrophotometer at 550 nm.

For cytochrome c, flavin adenine dinucleotide (FAD), nicotinamide adenine dinucleotide (NAD$^+$), 10 µM cytochrome c (manufactured by Sigma), 1 mM FAD (manufactured by Sigma), or 1 mM NAD$^+$ (manufactured by Sigma) was dissolved in the hydrogen water. After reaction at room temperature for 30 minutes, absorbance at 415, 400, and 340 nm, respectively, were measured with a spectrophotometer. The results are shown in Table 1. In Table 1, the eliminated amount is indicated as a value obtained by subtracting the amount of each molecular species remaining after the reaction in the hydrogen water from the amount of each molecular species remaining after the reaction in hydrogen-free water as 100%.

The measurement results shown in Table 1 demonstrate things described below. Specifically, it could be confirmed that the hydrogen water eliminates the most highly reactive and highly toxic hydroxyl radicals, peroxynitrite, and lipid peroxyl radicals through reduction. On the other hand, the elimination of NO, superoxide, hydrogen peroxide, and the like known to be used in signal transduction and so on in vivo was not observed. Likewise, the hydrogen water did not have any influence on cytochrome c, FAD, and NAD$^+$ that play a central role in in vivo energy metabolism through oxidation-reduction reactions.

TABLE 1

| | Eliminated amount (%) |
|---|---|
| Active oxygen species | |
| NO | <1 |
| ONOO$^-$ | 97 |
| $H_2O_2$ | <1 |
| •OH | 69 |
| ROO• | 37.6 |
| $O_2^-$• | <1 |
| Respiratory chain-related molecular species | |
| Cytochrome c | <1 |
| FAD | <1 |
| NAD+ | <1 |

*The eliminated amount is indicated as a value obtained by subtracting the amount of each molecular species remaining after the reaction in the hydrogen water from the amount of each molecular species remaining after the reaction in hydrogen-free water as 100%.

Example 2

Antimycin A, which is an inhibitor of mitochondrial respiratory chain complex III, promotes reactive oxygen species production in cells and induces oxidative stress-induced cell death as a result. Thus, in Example 2, the defensive effects of hydrogen against oxidative stress in the presence of antimycin A was measured.

Preparation of Hydrogen-Containing Medium

A cell culture medium requires containing oxygen, being almost neutral, and containing no metal ions with a high concentration. For preparing a culture medium containing oxygen and hydrogen molecules coexisting with each other, it can be predicted to separately dissolve these molecules under pressure according to the Henry's law. The space in the hydrogen pressure device is filled with oxygen. Then, hydrogen gas is compressed to 5 atm. The partial pressure of oxygen gas can be kept at 1 atm. Therefore, an oxygen concentration necessary for culture can be secured. Penicillin G (manufactured by Invitrogen) at a final concentration of 100 units/mL and streptomycin (manufactured by Invitrogen) at a final concentration of 100 µg/mL were allowed to be contained in 1 l of Dulbecco's Modified Eagle Medium (DMEM; manufactured by Invitrogen) as a cell culture medium. This mixture was injected into a 5-l pressure-resistant bottle. Then, hydrogen gas was charged thereinto at a pressure of 0.4 MPa. After 2 hours, DMEM supplemented with hydrogen was collected from the bottle under reduced pressure.

Alternatively, when hydrogen with a high concentration was unnecessary, a hydrogen-containing medium having an almost equal amount of dissolved oxygen to that in DMEM before hydrogen addition was prepared by the addition of an appropriate amount of oxygen-saturated DMEM. The dissolved oxygen was kept at a constant level by measuring a dissolved oxygen concentration in DMEM as a culture solution by use of Mitocell MT200 (manufactured by CT and C Co., Ltd.). A hydrogen content was analyzed using the dissolved hydrogen measuring apparatus. One example of results of measuring dissolved oxygen and dissolved hydrogen concentrations in the prepared hydrogen-containing DMEM is shown in Table 2. Horse serum (manufactured by PAA, Austria) was added at a final concentration of 1% to this medium to prepare a hydrogen-containing medium adjusted to a dissolved hydrogen concentration of 0.6 to 0.8 mM and a dissolved oxygen concentration of 8.6 to 9.3 mg/L. This hydrogen-containing medium was used in subsequent experiments.

TABLE 2

| DMEM | Dissolved oxygen (mg/L) | Dissolved hydrogen (mM) |
|---|---|---|
| Before hydrogen charging | 8.86 | 0 |
| After hydrogen charging (1) | 5.73 | 0.7 |
| Oxygen saturation (2) | 32.0 | 0 |
| Hydrogen-containing medium* | 8.89 | 0.6 |

*(2) was added in an amount of approximately 1/10 to (1).

Culture of Rat Adrenal Gland-Derived Pheochromocytoma PC12 Strains

Rat adrenal gland-derived pheochromocytoma PC12 strains were suspended in DMEM containing 10% fetal bovine serum (manufactured by EQUITECH-BIO, USA) and 5% horse serum and seeded at a cell density of $1 \times 10^4$ cells/$cm^2$ in a collagen-coated cell culture dish. The cells were cultured with an incubator at 37° C. under 5% $CO_2$. To confirm the effects of the hydrogen-containing medium, the medium was aspirated after overnight culture, and the cells were washed once with DMEM containing 1% horse serum and used in subsequent experiments.

The culture dish in an open system was used in cell culture using the hydrogen-containing medium. In this case, the cell culture was designed as follows to prevent hydrogen from being released from the culture solution: 2 l of hydrogen water with an appropriate concentration was placed in a 3-l plastic container. A table was placed on the water surface, and the dish during culture using the hydrogen-containing medium was left standing thereon. The cells were cultured at 37° C. in a sealed state. Hereinafter, the use of hydrogen water was in line with this method. A dish during culture using hydrogen-free medium was left standing on a table in a plastic container containing untreated water instead of the prepared hydrogen water. The cells were cultured at 37° C.

Examination of Inhibitory Effects of Hydrogen on Cell Death Induced by Antimycin A To measure the defensive effects of hydrogen against oxidative stress, PC12 cells were cultured on a collagen-coated 24-well cell culture dish (manufactured by IWAKI&Co. Ltd.). Then, 2 mL of hydrogen-containing medium supplemented or unsupplemented with antimycin A (manufactured by Sigma) was added to each well. After 24 hours, the number of viable cells having a pyramid-shaped cell form was counted under a phase contrast microscope. In this experiment, hydrogen-free DMEM containing 1% horse serum (hereinafter, referred to as hydrogen-free medium) was used as a comparative control. A phase contrast microscopic image after 24 hours is shown in FIG. 1.

Figure 2:
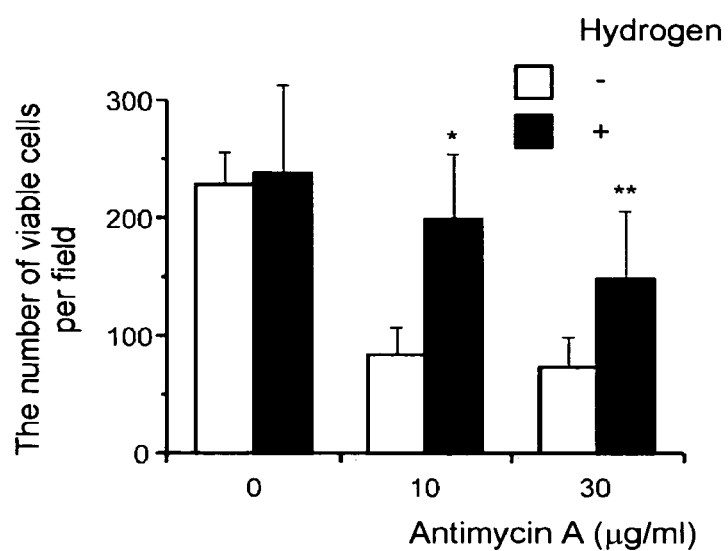
FIG. 2 is a graph where the number of viable PC12 cells is compared between a hydrogen-containing medium and a hydrogen-free medium after antimycin A treatment.

Among the cells cultured in the hydrogen-free medium supplemented with 10 µg/mL antimycin A, many dead cells that were round in shape and small in size were observed, and the number of pyramid-shaped viable cells was reduced. By contrast, in the hydrogen-containing medium supplemented with 10 µg/mL antimycin A, the number of dead cells was smaller, and the proportion of viable cells was significantly increased as compared with the hydrogen-free medium. Results of counting the numbers of viable cells in the hydrogen-containing medium and the hydrogen-free medium at varying antimycin A concentrations are shown in FIG. 2. The bar graph shows an average of at least 4 wells, and the error bars denote standard deviation. The number of viable cells in the hydrogen-containing medium was significantly increased at both antimycin A concentrations of 10 µg/mL and 30 µg/mL, demonstrating the cell death inhibitory effects of hydrogen addition.

Example 3

Figure 3:
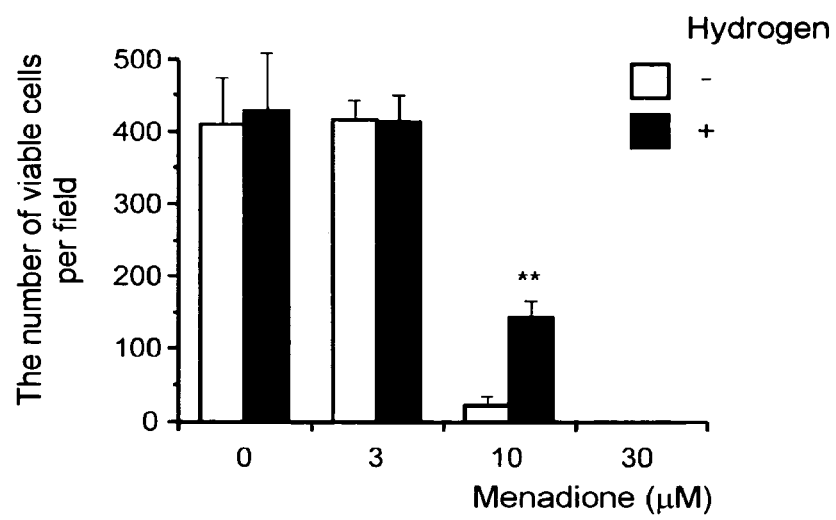
FIG. 3 is a graph where the number of viable PC12 cells is compared between a hydrogen-containing medium and a hydrogen-free medium after menadione treatment.

Examination of Inhibitory Effects of Hydrogen on Cell Death Induced by Menadione Menadione, which is an inhibitor of mitochondrial respiratory chain complex I, promotes reactive oxygen species production in cells and induces oxidative stress-induced cell death as a result. Thus, to measure the defensive effects of hydrogen against oxidative stress as in the experiment on antimycin A-induced cell death shown in Example 2, PC12 cells were cultured in a collagen-coated 24-well cell culture dish. Then, 2-ml of the hydrogen-containing medium supplemented or unsupplemented with menadione (manufactured by Sigma) at varying concentrations was added to each well. After 24 hours, the number of viable cells having a pyramid-shaped cell form was counted under a phase contrast microscope. In this experiment, a hydrogen-free medium was used as a comparative control. The results are shown in FIG. 3. The bar graph shows an average of at least 4 wells, and the error bars denote standard deviation. The number of viable cells in the hydrogen-containing medium supplemented with 10 µM menadione was significantly increased, demonstrating the cell death inhibitory effects of hydrogen addition.

Example 4

Figure 4:
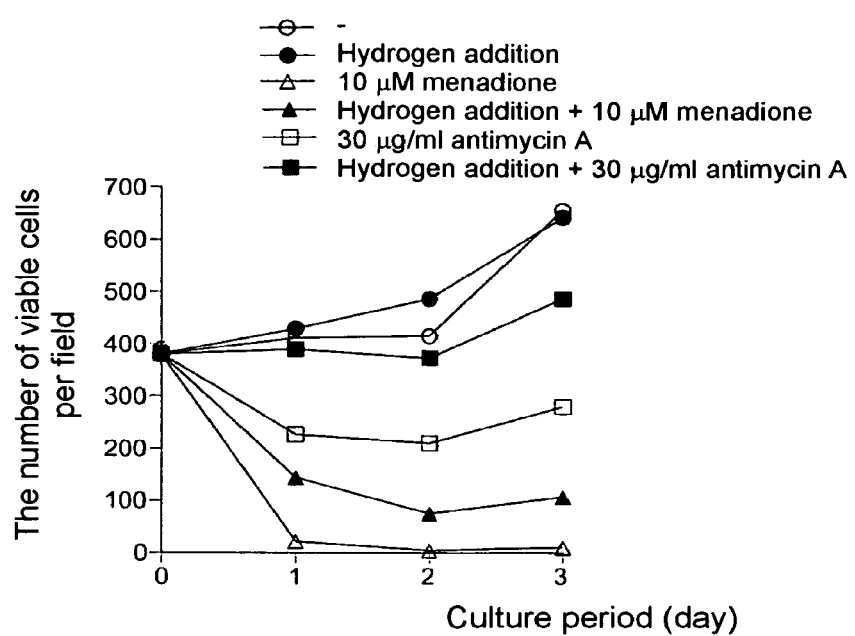
FIG. 4 is a graph showing time-dependent changes in the number of viable PC12 cells in a hydrogen-containing medium and a hydrogen-free medium after antimycin A or menadione treatment.

Time-Course Analyses of Inhibitory Effects of Hydrogen on Cell Death Induced by Antimycin A and Menadione The defensive effects of hydrogen against oxidative stress in cell death induced by antimycin A and menadione were measured in time-course analyses in the same way as in Examples 2 and 3 to thereby examine the durability of the defensive effects of hydrogen. PC12 cells were cultured in a collagen-coated 24-well cell culture dish (manufactured by IWAKI&Co. Ltd.). Then, 2-ml of the hydrogen-containing medium supplemented or unsupplemented with 10 µM menadione or 30 µg/mL antimycin A was added to each well. After 0, 1, 2, and 3 days, the number of viable cells having a pyramid-shaped cell form was counted under a phase contrast microscope. The results are shown in FIG. 4. Each mark shows an average of at least 4 wells. The cell death inhibitory effects of hydrogen addition could be confirmed even on the 2nd day or later, demonstrating that the cell death inhibitory effects of hydrogen addition continues even on the 24th hour or later.

Example 5

Figure 5:
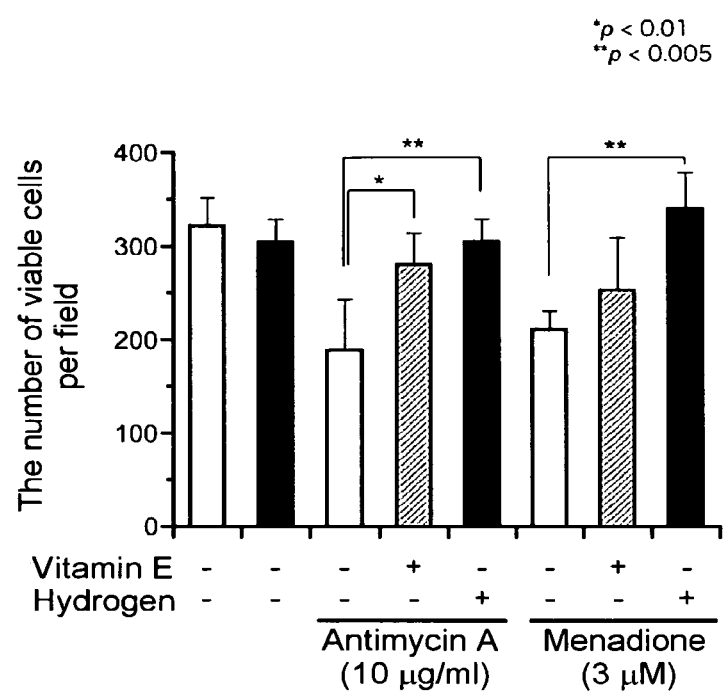
FIG. 5 is a graph where the number of viable PC12 cells is compared between a hydrogen-containing medium and a vitamin E-supplemented hydrogen-free medium after antimycin A or menadione treatment.

Comparative Measurement of Cell Death Inhibitory Effects of Hydrogen Relative to Vitamin E In Example 5, vitamin E, which has been well known as a substance exhibiting antioxidative effects and has been used widely, was compared with hydrogen. Cell death was induced by antimycin A or menadione in the same way as in Examples 2 and 3. The number of viable cells was compared between the hydrogen-containing medium and a hydrogen-free medium containing alpha-tocopherol (vitamin E). First, PC12 cells were cultured in a collagen-coated 24-well cell culture dish (manufactured by IWAKI&Co. Ltd.). Then, 2-ml of the hydrogen-containing medium supplemented or unsupplemented with 3 µM menadione or 10 µg/mL antimycin A or a hydrogen-free medium containing 100 µM alpha-tocopherol (manufactured by Sigma) was added to each well. After 24 hours, the number of viable cells having a pyramid-shaped cell form was counted under a phase contrast microscope. A hydrogen-free medium was used as a comparative control. The results are shown in FIG. 5.

The bar graph shows an average of at least 4 wells, and the error bars denote standard deviation. The number of viable cells in the hydrogen-containing medium was significantly increased as compared with the hydrogen-free medium. By contrast, inhibitory effects on cell death induced by antimycin A were observed, albeit weaker than those of hydrogen, in the hydrogen-free medium containing alpha-tocopherol, while significant effects on menadione were not observed therein. These results demonstrate that hydrogen is a more excellent anti-oxidative stress substance than vitamin E at a cellular level.

Example 6

Figure 6:
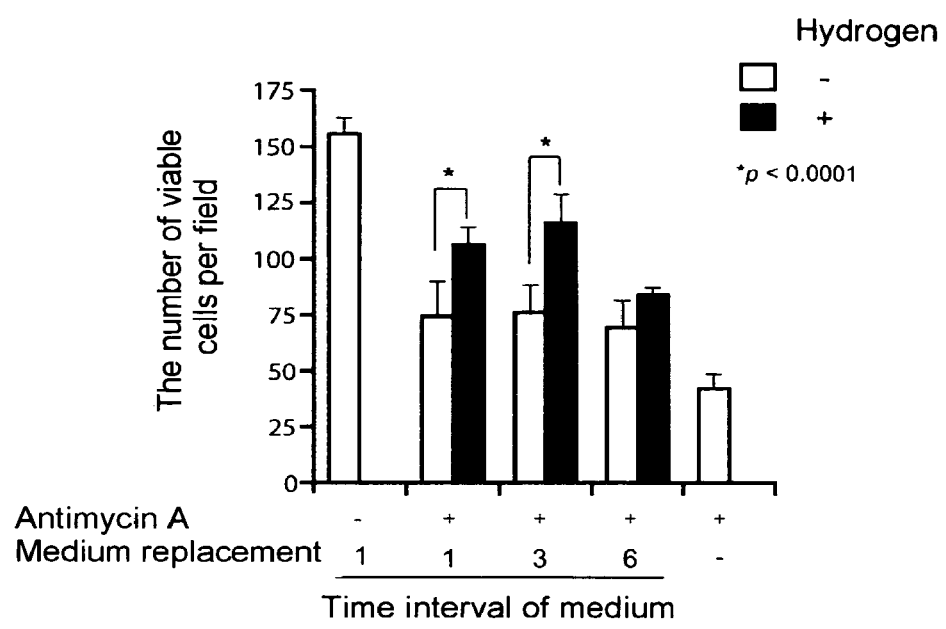
FIG. 6 is a graph where the number of viable PC12 cells is compared among replacements of a hydrogen-containing medium after antimycin A treatment.

Measurement of Inhibitory Effects of Hydrogen-Containing Medium Post-Addition on Cell Death Induced by Antimycin A To demonstrate that the inhibitory effects of the hydrogen-containing medium on cell death induced by antimycin A are not attributed to the degeneration of antimycin A by hydrogen but serve as the inhibition of oxidative stress induced by antimycin A, cells were treated with a hydrogen-free medium containing antimycin A. After a certain period of time, the hydrogen-free medium was replaced by the hydrogen-containing medium to examine the presence or absence of cell death inhibition. PC12 cells were cultured in a collagen-coated 24-well cell culture dish in the same way as in the experiment on antimycin A-induced cell death shown in Example 5. Two mL of hydrogen-free medium supplemented with 30 µg/mL antimycin A was added to each well. Then, the hydrogen-free medium was replaced by 2 mL of hydrogen-containing medium or hydrogen-free medium on the 1st, 3rd, and 6th hours. After 24 hours from antimycin A addition, the number of viable cells having a pyramid-shaped cell form was counted under a phase contrast microscope. The results are shown in FIG. 6.

The bar graph shows an average of at least 4 wells, and the error bars denote standard deviation. The number of viable cells in the replacements to the hydrogen-containing medium after 1 and 3 hours was significantly increased as compared with the hydrogen-free medium. Even the hydrogen supply after the addition of antimycin A can inhibit cell death, demonstrating that hydrogen inhibits oxidative stress secondarily caused by the addition of antimycin A. Moreover, the effects were not observed after 6 hours. This is presumably because irreversible cell death was already in process at this point in time and therefore killed cells at a certain rate, regardless of the presence or absence of hydrogen addition.

Example 7

Figure 7:
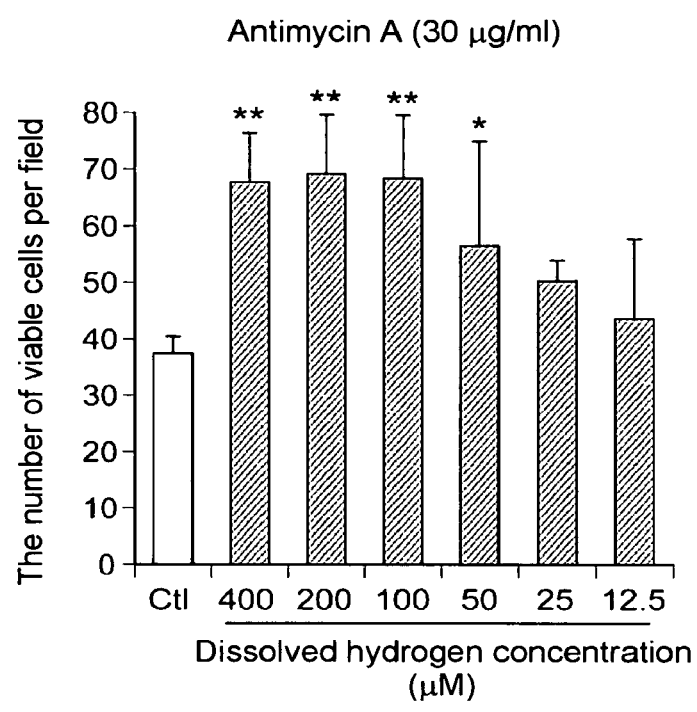
FIG. 7 is a graph showing the influence of changes in dissolved hydrogen concentration on the number of viable PC12 cells after antimycin A treatment.

Measurement of Influence of Dissolved Hydrogen Concentration on Cell Death Inhibitory Effects A hydrogen concentration necessary for defense against oxidative stress in cells was examined PC12 cells were cultured in a collagen-coated 24-well cell culture dish in the same way as in the experiment on antimycin A-induced cell death shown in Example 2. Two mL of a medium containing hydrogen at varying concentrations supplemented with 30 µg/mL antimycin A was added to each well. After 24 hours, the number of viable cells having a pyramid-shaped cell form was counted under a phase contrast microscope. The results are shown in FIG. 7. Cell death inhibition depended on hydrogen concentrations, demonstrating that the inhibitory effects are provided by hydrogen. Furthermore, cell death could be inhibited significantly even at a hydrogen concentration as low as 50 µM corresponding to approximately 1/16 of the saturated hydrogen concentration.

Example 8

Measurement of Inhibitory Effects of Hydrogen on Mitochondrial Dysfunction Caused by Oxidative Stress Antimycin A or the like accelerates oxidative stress, damaging mitochondrial functions. Thus, PC12 cells were cultured in a collagen-coated 35-mm glass bottom dish in the same way as in the experiment on antimycin A-induced cell death shown in Example 2. The hydrogen-containing medium containing 10 µg/mL antimycin A was added thereto. A hydrogen-free medium was used as a comparative control. After 50 minutes, a mitochondria-specific dye MitoTracker Green (final concentration: 1 µM; manufactured by Molecular Probe, USA) and a mitochondrial membrane potential-sensitive dye MitoTracker Red (final concentration: 100 nM; manufactured by Molecular Probe, USA) were added thereto, and the cells were cultured for another 10 minutes. Fluorescence images thereof at excitation wavelengths of 488 nm and 543 nm were observed with a confocal laser scanning microscope (manufactured by Olympus Corp.). The results are shown in FIG. 8.

Figure 8:
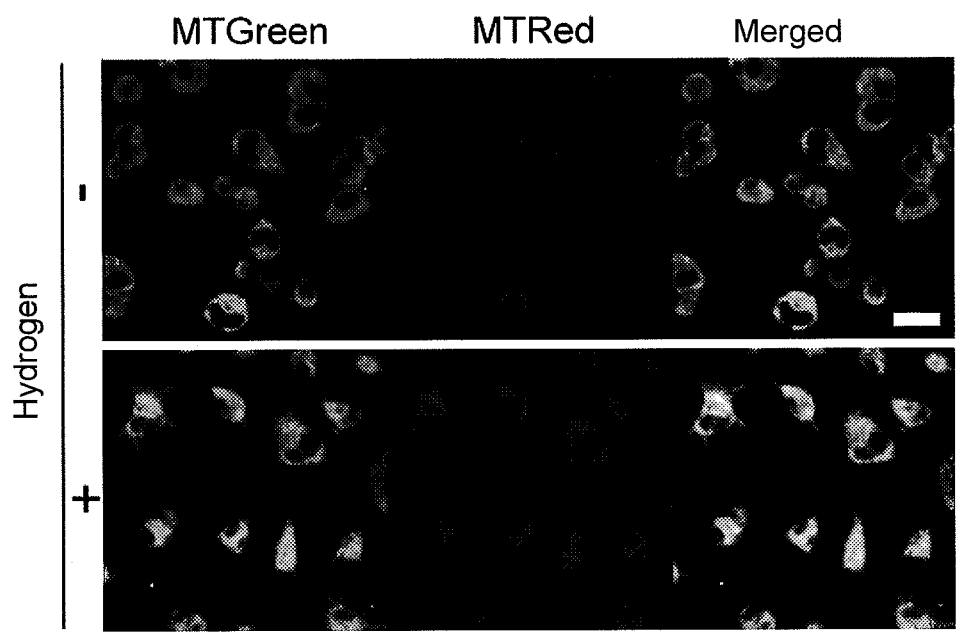
FIG. 8 is an image of mitochondria in antimycin A-treated PC12 cells in a hydrogen-containing medium.

In the experiment shown in FIG. 8, antimycin A (10 µg/ml) was added in the presence or absence of 0.6 mM hydrogen.

After 30 minutes, 1 μM MitoTracker Green (MTGreen) and 100 nM MitoTracker Red (MTRed) were added thereto, and the cells were cultured for another 10 minutes. Subsequently, cellular fluorescence was observed with a confocal laser scanning microscope. The scale bar in the diagram denotes 50 μm. Reductions in MTRed staining intensity in the absence of hydrogen indicate reductions in mitochondrial membrane potential. The merged images are rendered darker green in the absence of hydrogen than in the presence of hydrogen. This suggests that the hydrogen molecules passed through the mitochondrial membranes.

The antimycin A-treated cells in the hydrogen-free medium assume a mitochondrial form that is round in shape and is torn off, while the antimycin A-untreated cells assume a mitochondrial form with a reticular structure. Moreover, MitoTracker Red fluorescence intensity is also reduced. These results indicate decreases in mitochondrial functions. By contrast, the antimycin A-treated cells in the hydrogen-containing medium have both a form and MitoTracker Red fluorescence intensity close to those of the antimycin A-untreated cells, demonstrating that decreases in mitochondrial functions are inhibited. Specifically, the hydrogen molecules protected the mitochondria.

Example 9

Measurement of Effects of Hydrogen Water on Model Animals with Accelerated Oxidative Stress Transgenic mice expressing the inactive gene of aldehyde dehydrogenase 2 display accelerated oxidative stress and aging-related disease (C2 mice; WO2005/020681, A1). These C2 mice (5 week old, female, four individuals in each group) were permitted to freely ingest hydrogen water. In an open system, hydrogen is released and lost from the hydrogen water. Therefore, to keep hydrogen in a state dissolved in the water over a long time, 2 bearing balls were placed in an outlet for water ingestion to prevent the water from leaking out and coming into contact with air. The mice can poke at the bearing balls and drink the water from the outlet for water ingestion. The amount of water drunk by the mice was not reduced by this method as compared with in the open system. In this method, half or more of the hydrogen molecules remained even after 24 hours. Hydrogen water prepared by a method equivalent to that in Example 1 was charged into a 100-mL glass feed-water bottle to completely fill the bottle. The hydrogen water was replaced once 24 hours. Control water used was water obtained by eliminating hydrogen gas from the hydrogen water. This control water used was totally the same as the hydrogen water except for hydrogen dissolution.

Figure 9:
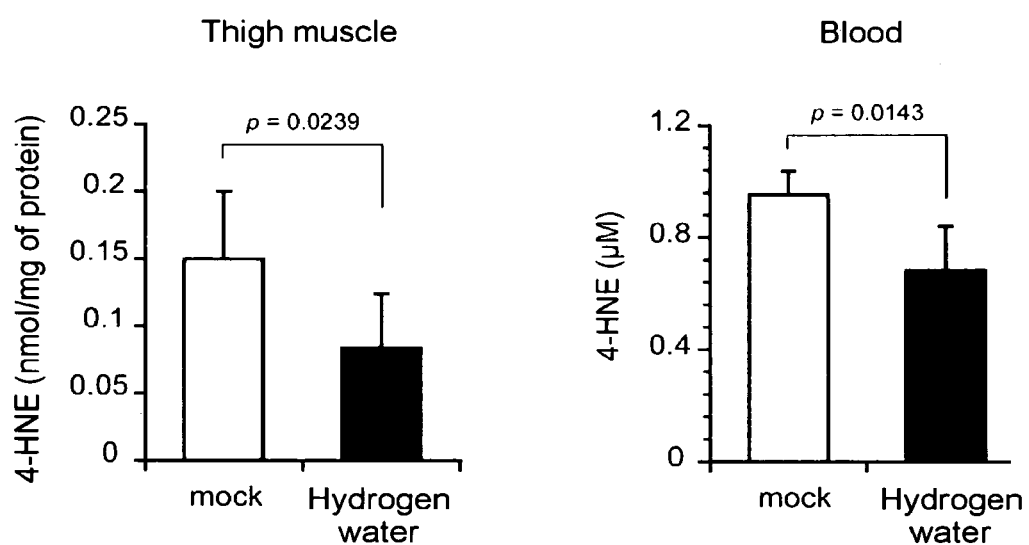
FIG. 9 is a graph showing the 4-HNE accumulation inhibitory effects of hydrogen water in model animals with accelerated oxidative stress.

The C2 mice were permitted to freely ingest the hydrogen or control water. Changes in the concentration of 4-hydroxy-2-nonenal (4-HNE), which is harmful aldehyde generated form lipid peroxide and serves as an indicator for in vivo oxidative stress accumulation, were measured in the blood and in the femoral muscle. After 4 weeks, the whole blood was collected from the eyeground. Moreover, the femoral muscle was immediately frozen with liquid nitrogen and stored at −80° C. The frozen organ was disrupted with a hammer. Then, 1 mL of ice-cold buffer (100 mM sodium chloride, 10 mM Tris-HCl, pH 7.2) was added to a 100 mg aliquot of the organ. Subsequently, this sample was cut finely with POLYTRON (manufactured by KINEMATICA AG, Switzerland). The cut samples were sonicated on ice for 1 minute after the addition of a ¼ amount of 10% SDS and then centrifuged at 3000 rpm at 4° C. The supernatant was collected and diluted with a buffer to 10 mg/mL in terms of the amount of proteins extracted to thereby prepare muscle extracts. 60 μL of whole blood and 200 μL of muscle extracts were used to measure a 4-HNE concentration with BIOXYTECH HAE-586 ASSAY KIT (manufactured by OXIS, USA) by a method described in the manufacturer's manual. The results are shown in FIG. 9. The amount of 4-HNE in the hydrogen water ingestion group was significantly reduced in both the blood and the femoral muscle. These results demonstrate that hydrogen ingested with a drink can inhibit in vivo oxidative stress in blood and in tissues.

Example 10

Figure 10:
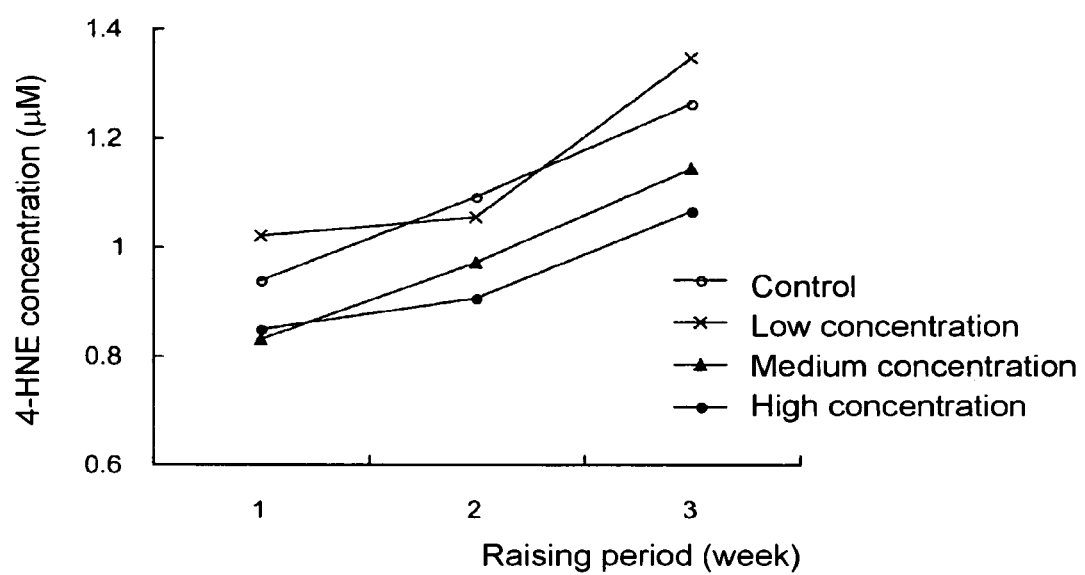
FIG. 10 is a graph showing time-dependent changes in the amount of 4-HNE accumulated in the blood of hydrogen water-administered model animals with accelerated oxidative stress.

Time-Dependent Analyses of Oxidative Stress Inhibitory Effects of Water with Varying Dissolved Hydrogen Concentrations C2 mice (4 week old, male, 4 to 5 individuals in each group) were permitted to freely ingest water with varying dissolved hydrogen concentrations according to Example 9. After 1, 2, and 3 weeks, 60 μL of blood was collected from the eyeground. The amount of 4-HNE was measured according to the method shown in Example 9. Hydrogen contents in the water provided thereto are high concentration (H: 1.6 to 1.2 mM), medium concentration (M: 0.7 to 0.9 mM), low concentration (L: 0.3 to 0.5 mM), and a control (C: 0 mM). No difference in the amount of hydrogen water drunk per mouse was observed among the groups. The results are shown in FIG. 10. Reductions in the amount of 4-HNE were observed on the 2nd week in the groups that ingested high-concentration and medium-concentration hydrogen water. However, such reductions were not observed for the low-concentration hydrogen water, demonstrating that the hydrogen water with an almost saturated concentration or higher is effective for oxidative stress inhibition. These results also demonstrated that the continuous drinking of the hydrogen water for approximately 2 weeks is effective for oxidative stress inhibition.

Example 11

Measurement of Ischemia-Reperfusion Injury Alleviating Effects of Hydrogen Gas Inhalation Mice (C57BL/6 line, 5 week old, male) were put under general anesthesia by supplying mixed anesthetic gases (oxygen: 0.3 L/min., nitrous oxide: 0.7 L/min., Sevofrane (Maruishi Pharmaceutical Co., Ltd.): 3%) thereto with a small animal general anesthesia machine Soft Lander (Neuroscience Inc.). After anesthesia introduction, the anesthesia was maintained for a long time by supplying thereto a mixed anesthetic gas containing Sevofrane at a concentration reduced to 1.5% (oxygen: 0.3 L/min., laughing gas: 0.7 L/min., Sevofrane: 1.5%). Surgical skills (reference: Yadav, S. S. et al., Transplantation 65, 1433-1436 (1998)) shown below were used to prepare model animals with local ischemia-reperfusion injury in the liver. The model animals were examined by hematoxylin-eosin staining (H&E staining) for tissue degeneration in the ischemic liver and hepatic parenchymal cell death induced by ischemia-reperfusion injury.

The belly was opened in the middle thereof. Three canals, portal vein, hepatic artery, and bile duct, leading to the left robe of the liver were together blocked (ischemia start) with a micro-clamp (FD562; Aesculap, South San Francisco, Calif., USA). The belly was sutured with a silk thread. After 90 minutes, the belly was opened again by removing the silk thread used for suture, and the micro-clamp was removed (reperfusion start). The belly was sutured again with a silk thread. The left robe of the liver was reperfused for 3 hours under anesthesia. Hydrogen gas was mixed with the mixed anesthetic gas and supplied to a hydrogen gas-supplied group at a designated hydrogen gas flow rate at designated times. To keep all the mixed gas flow rates at a constant level, the nitrous oxide flow rate was reduced by the hydrogen gas flow rate. After reperfusion for 3 hours, the left robe of the liver (ischemic liver) was excised and cut into fine strip slices. The slices were fixed by dipping in 10% neutral buffered formalin solution (Wako Pure Chemical Industries, Ltd.).

The fixed ischemic liver slices were subjected to dehydration with ethyl alcohol, dehydrating agent removal with xylene, and paraffin infiltration in an automatic embedding apparatus (SAKURA, Tissue-Tek VIPS). The paraffin-embedded ischemic liver was cut into slices of 3 μm to 5 μm in thickness with a sledge microtome. The slices were attached to slide glass. The paraffin was removed by treatment with xylene and then with ethyl alcohol, and the slices were washed with running water. The slices were hematoxylin-stained with a Mayer's hematoxylin solution (Wako Pure Chemical Industries, Ltd.) and then washed with water. Subsequently, the slices were eosin-stained with 1% eosin Y solution (Wako Pure Chemical Industries, Ltd.). After complete dehydration with ethyl alcohol, the slices received xylene penetration and were covered with cover glass coated with a mounting agent Malinol (Muto Pure Chemicals Co., Ltd.) to prepare a permanent preparation.

Figure 11:
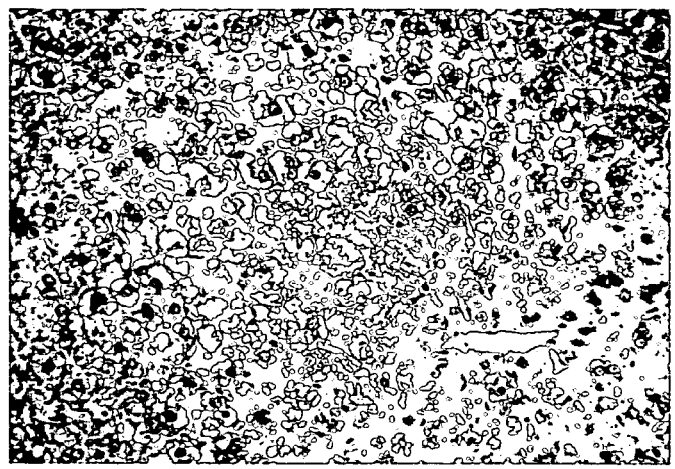
FIG. 11 is an image of hematoxylin-eosin-stained liver slices showing the ischemia-reperfusion injury alleviating effects of hydrogen gas inhalation.
Figure 11:
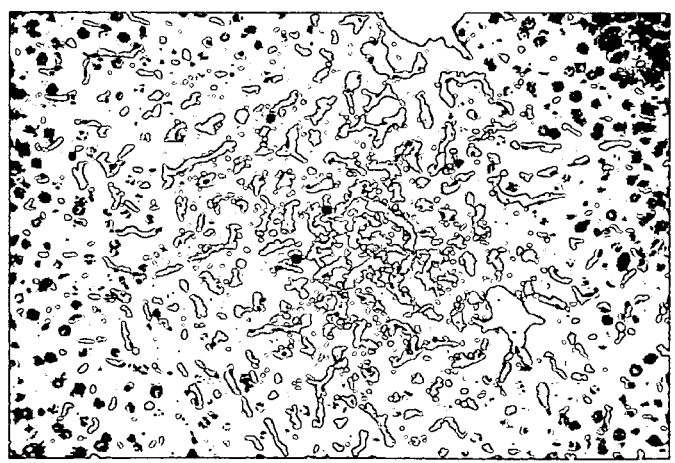

The results are shown in FIG. 11 and Table 3.

TABLE 3

| Hydrogen gas flow rate (L/min.) Hydrogen gas inhalation period | | Degenerated region in liver tissues (%) |
|---|---|---|
| 0 | | 74 |
| 0.2 | From 5 minutes before reperfusion start to 5 minutes after reperfusion start (10 minutes in total) | 10 |
| 0.1 | From 5 minutes before reperfusion start to 5 minutes after reperfusion start (10 minutes in total) | 20 |
| 0.04 | From 10 minutes before reperfusion start through whole reperfusion period (280 minutes in total) | 26 |

In FIG. 11, cytoplasmic degeneration (which is not stained red with eosin and leaves a white patch) in many cells occurs in the hydrogen gas-untreated liver tissues. Furthermore, many cells in the hydrogen gas-untreated liver tissues lost their nuclei (which are stained purple with hematoxylin). Both nuclear and cytoplasmic degenerations less occurred in the liver tissues of the mice that inhaled hydrogen gas (0.2 L/min.) for 10 minutes from 5 minutes before reperfusion start to 5 minutes after reperfusion start. These tissues were maintained favorably. The data of Table 3 shows the proportion of degenerated regions to the whole slice area as 100% obtained by measuring the area of the degenerated regions (regions with a white patch) in the liver tissues from the digital photograph of the whole slice by use of image processing software NIH Image. Hydrogen gas inhalation alleviated degeneration in the liver tissues in all the cases. It has been revealed that ischemia-reperfusion injury is caused by the effects of free radicals. Therefore, these results demonstrated that the hydrogen gas inhalation eliminated the free radicals. It can be inferred by analogy that hydrogen gas inhalation, in general, not only alleviates ischemia-reperfusion injury but also eliminates free radicals. Hydrogen generates no fire under 4% hydrogen conditions and can be utilized safely.

Example 12

Measurement of Eliminating Effects of Hydrogen Ingestion on Free Radicals after Exercise It has been known that strenuous exercise and the sudden stop of exercise generate free radicals and damage various tissues including muscles. Hydrogen water ingestion and hydrogen gas inhalation exhibited eliminating effects on free radicals after exercise. Rats (Wister Rats, 8 week old, male) were run at a speed of 40 m/min. for 20 minutes. Immediately afterward, the rats inhaled air containing 10% hydrogen gas for 30 minutes. Alternatively, the rats received intraperitoneal injection with a saline containing supersaturated hydrogen and were laid to rest for 30 minutes. After 30 minutes, the rats were slaughtered. The skeletal muscle was excised. From H&E staining, the hydrogen inhalation was confirmed to alleviate damage in the muscular tissues. Furthermore, deletion mutation in mitochondrial DNA was detected by a PCR method, indicating that deletion in mitochondrial DNA was reduced in the rats that ingested hydrogen. These results demonstrated that hydrogen ingestion maintains muscular tissues after strenuous exercise. The method was conducted according to Sakai, Y., Iwamura, Y., Hayashi, J., Yamamoto, N., Ohkoshi, N., Nagata, H., Acute exercise causes mitochondrial DNA deletion in rat skeletal muscle., Muscle and Nerve 22: 256-261, 1999.

Example 13

Figure 12:
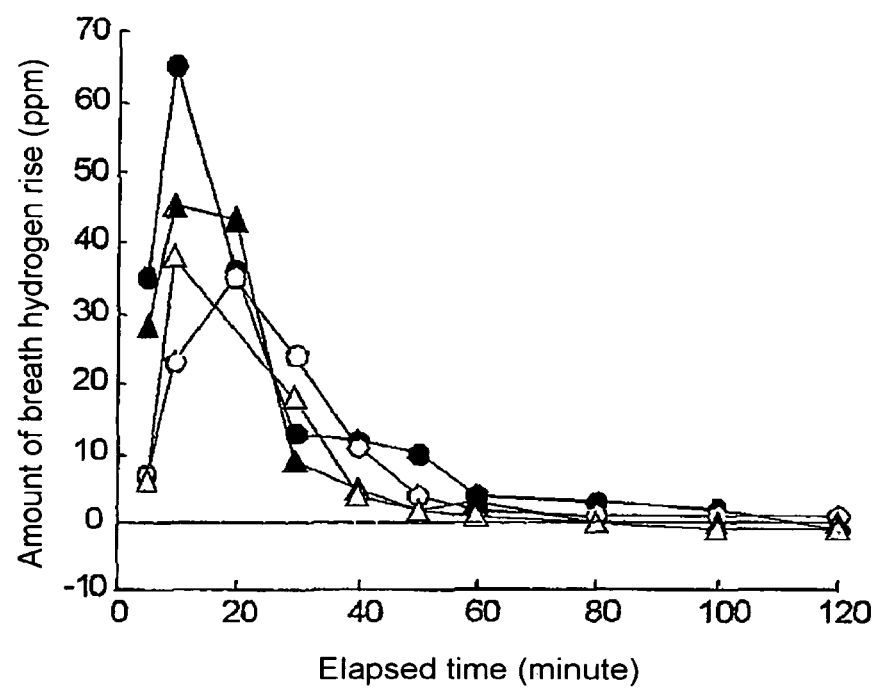
FIG. 12 is a graph showing time-dependent changes in the breath hydrogen concentrations of 4 persons resulting from the drinking of hydrogen water.

Demonstration that Hydrogen Molecules are Taken Up into Living Bodies by Drinking of Hydrogen Water and by Hydrogen Gas Inhalation To examine whether hydrogen molecules are actually taken up into living bodies by the ingestion of water containing dissolved hydrogen or by hydrogen gas inhalation, a human breath hydrogen concentration was examined A breath hydrogen concentration differs among individuals. Therefore, four subjects with a breath hydrogen concentration of 10 ppm or lower were targeted by the experiment. A breath hydrogen concentration before hydrogen water ingestion was measured with Breath Gas Analyzer (breath hydrogen analyzer) TGA-2000 (TERAMECS CO., LTD., Kyoto, Japan). Then, the subjects ingested 10 mL of hydrogen water per kg of body weight by drinking. Then, the subjects rinsed their mouth with hydrogen-free water to completely remove the hydrogen water. Time-dependent changes of breath hydrogen concentration were measured. The breath hydrogen concentration, though differing among individuals, was increased by 30 ppm or more within 20 minutes after hydrogen water ingestion and then reduced. Even after 1 hour, the high value was kept as compared with before hydrogen water ingestion, demonstrating that hydrogen was taken up into the living bodies, dissolved in blood, and excreted as breath from the lung. These results demonstrated that hydrogen was taken up into living bodies within approximately 20 minutes after hydrogen water ingestion and dissolved in blood. The results are shown in FIG. 12.

In this experiment, the hydrogen molecules were taken up into living bodies by the drinking of hydrogen water. By contrast, when subjects inhale hydrogen gas, for example, a method can be adopted wherein air and hydrogen gas was supplied separately or as a mixture prepared in advance into a gas inhalation mask for covering the mouth and nose of the subjects and inhaled by the subjects, or wherein air and hydrogen gas was supplied separately or as a mixture prepared in advance into a sealed container and inhaled by the subjects lying in a bed within the sealed container. In this case, hydrogen gas concentrations of approximately 4 vol % or lower are in no danger of fires or explosion.

Example 14

Figure 13:
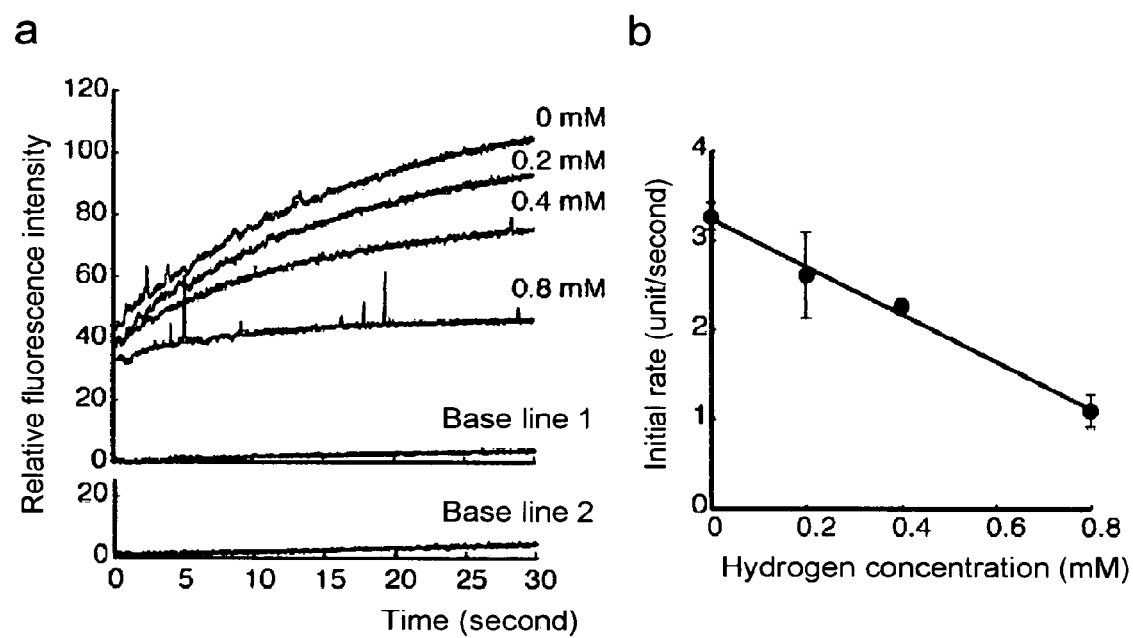
FIG. 13 is a diagram showing the removal of hydroxyl radicals by dissolved hydrogen molecules at room temperature under neutral conditions.

Whether hydrogen molecules in a simple solution state reduce biological substances was examined A neutral solution saturated with hydrogen molecules does not reduce, at room temperature, $NAD^+$, FAD, $Fe^{3+}$, $Cu^{2+}$, and oxidized cytochrome c containing trivalent heme iron. Specifically, the hydrogen molecules are stable in a solution without disrupting oxidation-reduction reactions. Moreover, the hydrogen molecules do not reduce hydrogen peroxide, nitrogen monoxide, or $O_2^-$. under this condition. These results indicate that the hydrogen molecules do not neutralize such reactive oxygen species that have main functions in signal transduction. By contrast, the hydrogen molecules, as shown in FIG. 13, reduce hydroxyl radicals (.OH) levels without catalysts under the same condition as above. FIG. 13 shows the removal of .OH by dissolved hydrogen molecules at room temperature under neutral conditions. The .OH was monitored with a spectrofluorometer. FIG. 13a shows typical changes over time in 2-[6-(4'-hydroxy)phenoxy-3H-xanthen-3-on-9-yl] benzoic acid (HPF) fluorescence intensity at each hydrogen molecule concentration. The base lines 1 and 2 denote changes in hydrogen peroxide-free (1) and ferrous perchlorate-free (2) HPF fluorescence intensities, respectively, at a hydrogen concentration of 0.8 mM. FIG. 13b shows results of determining an average value of initial reaction rates and standard deviation from 4 independent experiments .OH generated by the Fenton reaction was monitored with HPF fluorescence. HPF can specifically detect .OH without detecting hydrogen peroxide or $O_2^-$..

Example 15

Figure 14:
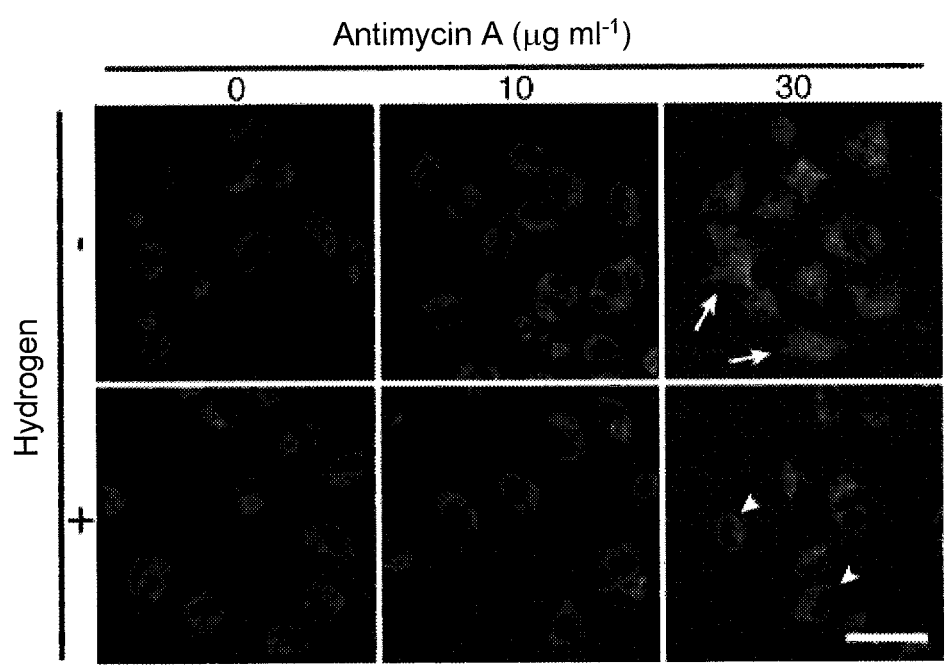
FIG. 14 is a diagram showing the removal of hydroxyl radicals by hydrogen molecules in PC12 cells and showing results of observing HPF fluorescence with a confocal laser scanning microscope.
Figure 15:
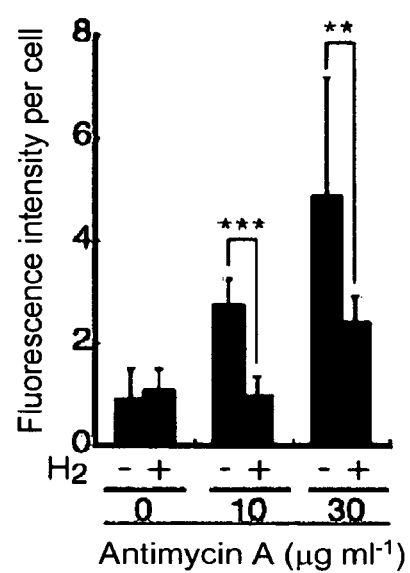
FIG. 15 is a graph showing the removal of hydroxyl radicals by hydrogen molecules in PC12 cells and showing results of quantifying HPF fluorescence intensity.

Whether hydrogen molecules can neutralize .OH in cultured cells was examined Spontaneously generated .OH does not reach an amount that exhibits cytotoxicity and is difficult to detect. Therefore, .OH was induced by two different methods. In this context, .OH was detected with a confocal laser scanning microscope by using HPF as a marker dye. First, hydrogen-saturated and oxygen-saturated media were prepared and mixed at their respective appropriate concentrations, with the concentrations monitored in hydrogen and oxygen electrodes. Subsequently, this mixed medium was replaced by a PC12 cell medium. Furthermore, the cells were placed in a container filled with gases adjusted to appropriate hydrogen and oxygen concentrations. In the PC12 cells, $O_2^-$. was generated by the addition of antimycin A, a mitochondrial respiratory chain inhibitor, and .OH levels were increased through the Fenton reaction. The treatment thereof with hydrogen molecules reduced .OH levels, as shown in FIGS. 14 and 15. FIG. 14 shows results of observing HPF fluorescence with a confocal laser scanning microscope after 30 minutes of antimycin A addition in the presence or absence of 0.6 mM hydrogen. The arrows and pikes denote cells with HPF fluorescence-positive and HPF fluorescence-negative nuclei, respectively. The scale bar denotes 50 µm. FIG. 15 shows results of quantifying HPF fluorescence intensity after antimycin A addition in the presence or absence of 0.6 mM hydrogen. The values were measured as to 100 cells in each independent experiment using NIH Image software. The cells were cultured in a sealed container with an appropriate gas concentration to maintain the initial hydrogen concentration. Interestingly, the hydrogen molecules reduced .OH levels in the nuclei (indicated by the pikes in the right panel of FIG. 14).

Furthermore, antimycin A was added to cells in the presence or absence of 0.6 mM hydrogen. After culture for 24 hours, the cells were stained with anti-8-OH-G and anti-HNE antibodies and observed with a confocal laser scanning microscope. The results are shown in FIGS. 16 to 19. The scale bars in FIGS. 16 and 18 denote 100 µm. Immunostaining intensities with anti-8-OH-G (FIG. 17) and anti-HNE (FIG. 19) antibodies were quantified using NIH Image software. In the experiments, the results of which are shown in FIGS. 14 to 19, antimycin A (+), hydrogen (+), and vitamin E (+) concentrations were 10 µg/ml, 0.6 mM, and 0.1 mM, respectively. Average values and standard deviations were determined from 4 independent experiments. *$P<0.05$, $P<0.01$, *$P<0.001$.

Figure 16:
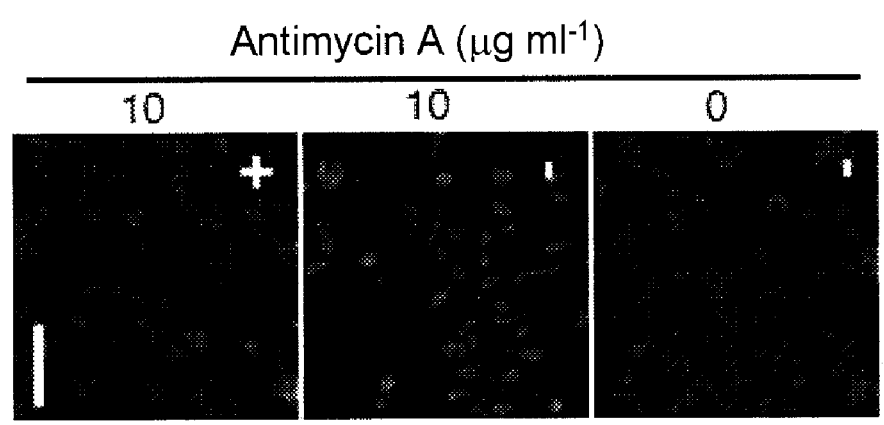
FIG. 16 is a diagram showing PC12 cells in which guanine oxidation has been inhibited by hydrogen molecules.
Figure 17:
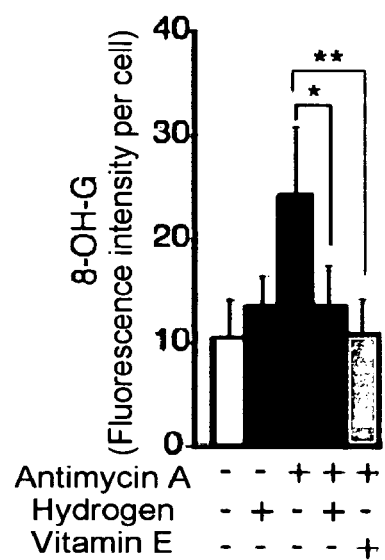
FIG. 17 is a graph showing the inhibition of guanine oxidation in PC12 cells by hydrogen molecules.
Figure 18:
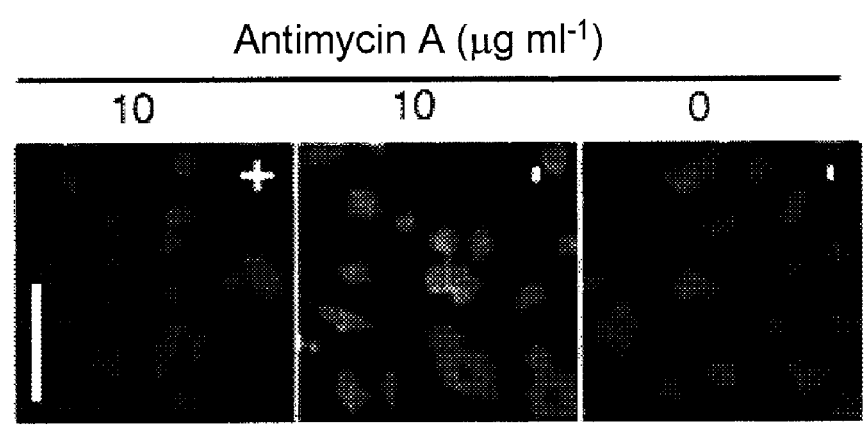
FIG. 18 is a diagram showing PC12 cells in which HNE production has been inhibited by hydrogen molecules.
Figure 19:
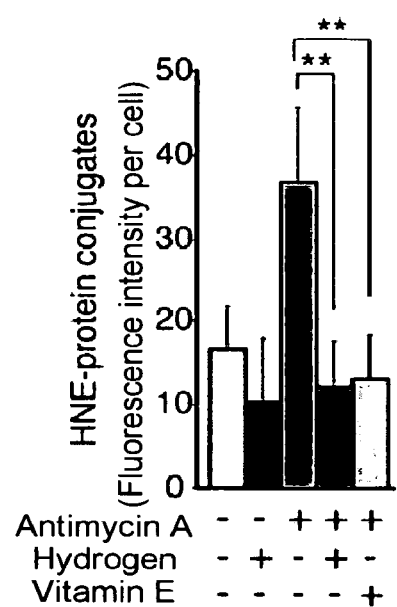
FIG. 19 is a graph showing the inhibition of HNE production in PC12 cells by hydrogen molecules.
Figure 22:
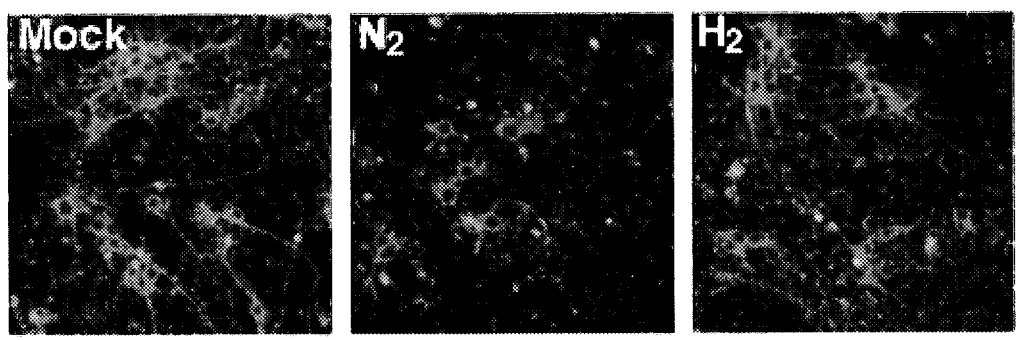
FIG. 22 is a diagram showing the increasing effects of hydrogen molecules on the number of viable neuronal cells.

As seen from reductions in oxidized guanine (8-OH-G) level in FIGS. 16 and 17, the hydrogen molecules protected nuclear DNA from oxidation. Moreover, the inhibition of accumulation of 4-hydroxy-2-nonenal (HNE), a final product of lipid peroxide, by the hydrogen molecules, as shown in FIG. 22, demonstrates that the hydrogen molecules also inhibit lipid peroxidation.

Example 16

Rat cerebral cortex-derived primary cultured cells were used to induce oxidative stress under more physiological conditions. It has been known that a rapid shift from ischemia to reperfusion causes an oxidative stress-induced disorder. Thus, the cells were exposed to an oxygen-glucose-deficient state mimicking ischemia for 60 minutes in a nitrogen or hydrogen atmosphere.

Rat cerebral cortex-derived primary cultured neuronal cells were prepared from a 16-day-old fetus. The cerebral cortex was cut after meninges removal and digested with a protease mixed solution (SUMILON). The slices were mechanically dissociated with a pipette. Then, the cells were dispersed in a nerve cell culture medium (SUMILON) and seeded at a cell density of $5 \times 10^4$ cells/cm² in a plate coated with poly-L-lysine. The medium was replaced every three days by Neurobasal Medium (Gibco) containing B-27 (Gibco). The cells cultured for 11 days were used in the experiment. One day before the creation of an oxygen-glucose-deficient state, the medium was replaced by Neurobasal Medium (Gibco) containing B-27 minus AO (Gibco). Quality control for the neuronal cells was confirmed by staining with neuron-specific anti-TUJ-1 and astrocyte-specific anti-GFAP antibodies. 90% or more of the cells were neuronal cells.

To initiate an oxygen-glucose-deficient state, the cell medium was replaced by a glucose-free DMEM medium aerated with 95% nitrogen/5% carbon dioxide or 95% hydrogen/5% carbon dioxide. This medium was left at 30° C. for 1 hour in 95% nitrogen/5% carbon dioxide or 95% hydrogen/5% carbon dioxide atmosphere. To terminate the oxygen-glucose-deficient state, the medium was replaced again by the medium used before replacement. Culture was further continued at 37° C. in 95% air/5% carbon dioxide atmosphere.

Figure 20:
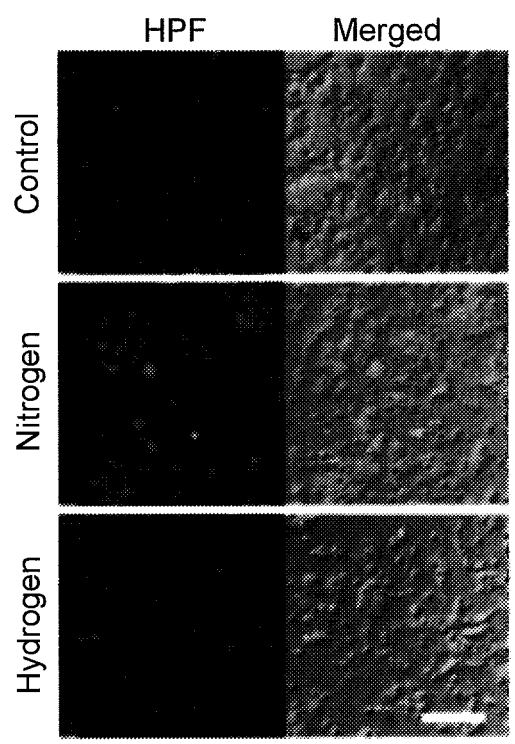
FIG. 20 is a diagram showing the neuronal cell protective effects of hydrogen molecules against in vitro ischemia and showing results of staining cells with HPF after 10 minutes of reperfusion.
Figure 21:
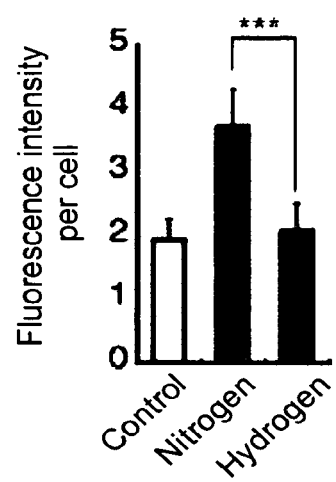
FIG. 21 is a graph showing the neuronal cell protective effects of hydrogen molecules against in vitro ischemia and showing results of measuring HPF fluorescence intensity as to 100 cells by using NIH Image software.

After 10 minutes of the termination of the oxygen-glucose-deficient state, the amount of .OH was measured based on HPF fluorescence. As a result, significant increases in the amount of .OH were observed in the absence of hydrogen but not observed in the presence of hydrogen, as shown in FIGS. 20 and 21. FIG. 20 shows results of staining the cells with HPF after 10 minutes of reperfusion (the left panels show fluorescence images, and the right panels show fluorescence images superimposed on Nomarski differential interference images). To prepare a control, cells were treated with a DMEM medium containing glucose and oxygen, instead of being exposed to an oxygen-glucose-deficient state. The scale bar in the diagram denotes 100 µm. FIG. 21 shows results of measuring HPF fluorescence intensity as to 100 cells by use of NIH Image software. An average value and standard deviation was determined from 4 independent experiments. **$P<0.01$.

Figure 23:
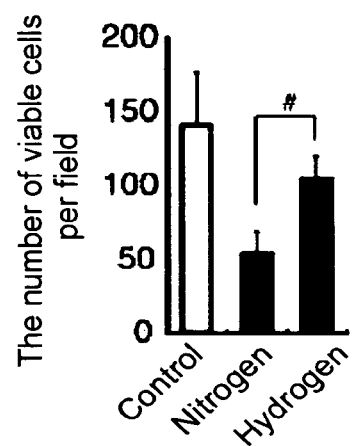
FIG. 23 is a graph showing increases in the viability of neuronal cells by hydrogen molecules in terms of the number of living cells.
Figure 24:
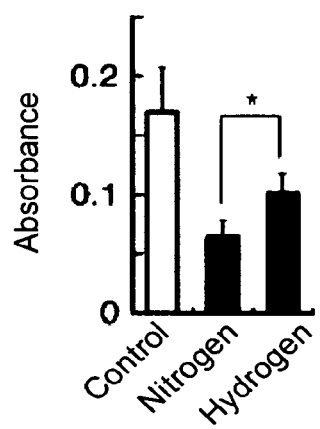
FIG. 24 is a graph showing increases in the viability of neuronal cells by hydrogen molecules in terms of mitochondrial enzyme activity.

After 1 day of oxygen-glucose deficiency, the viable neuronal cells were further detected by staining neuron-specific anti-TUJ-1 antibody. As a result, the hydrogen molecules increased the number of viable neuronal cells, as shown in FIG. 22. Moreover, the hydrogen molecules also increased their viabilities, as shown in FIGS. 23 and 24. FIG. 23 shows results of counting the number of viable nerve cells in a certain field under a phase contrast microscope after 1 day from the oxygen-glucose-deficient state. FIG. 24 shows results of measuring cell viability by a modified MTT method. Average values and standard deviations shown in FIGS. 23 and 24 were determined from 4 independent experiments. #$<0.0001$ in FIG. 23, *$P<0.05$ in FIG. 24. These results demonstrate that the hydrogen molecules inhibit oxidative stress-induced cell death.

Example 17

To examine whether hydrogen molecules as an antioxidant can be applied to medical care, examination was conducted using rat ischemic models.

In cerebral ischemia, diverse mechanisms generate reactive oxygen species, and .OH is detected after ischemia-reperfusion. Rats were rendered locally ischemic for 90 minutes by mild cerebral artery occlusion and subsequently reperfused for 30 minutes. During this period, the rats kept inhaling hydrogen, unless otherwise specified. FK506 (1 mg/kg of body weight) was administered into the blood once immediately before reperfusion. Edaravone (3 mg/kg of body weight) was administered into the blood twice immediately before reperfusion and immediately after reperfusion. After anesthesia, the rats were maintained at 20° C. under usual air. The rats inhaled hydrogen molecules for 120 minutes in total, unless otherwise specified. The rats inhaled a mixed gas of nitrous oxide (for anesthesia), oxygen, and hydrogen at ratios of 66 to 70%, 30%, and 0 to 4% (v/v), respectively. After 1 day of mild cerebral artery occlusion, the brain was sliced, and the slices were stained with 2,3,5-triphenyltetrazolium salt (TTC) capable of serving as a substrate in mitochondrial respiration process. After 1 week, the animals were put under anesthesia. Then, the brain was rapidly excised and fixed with 10% formalin. The paraffin-embedded brain was sliced into a thickness of 6 µm, and the slices were stained with hematoxylin-eosin. Moreover, VECSTAIN ABC Kit was used in staining with antibodies. Anti-Iba-I antibodies were purchased from Wako Pure Chemical Industries, Ltd. Image analysis software (Mac Scope ver. 2.55; Mitsuya Shoji) was used in slide analysis. All the animal experiments were conducted according to the guideline of the animal commission of Nippon Medical School.

Figure 25:
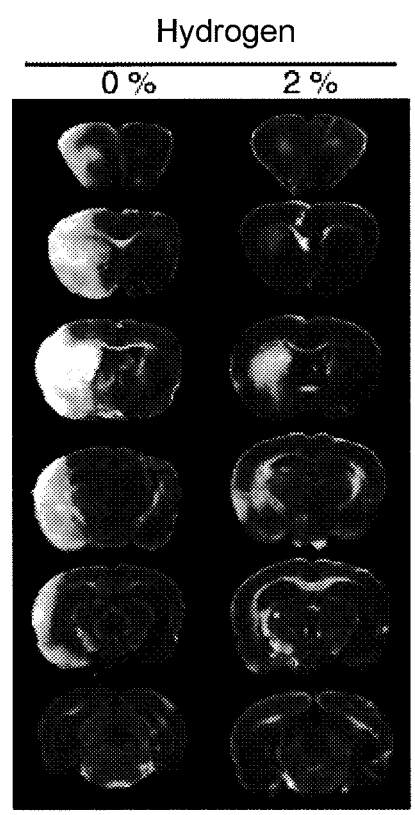
FIG. 25 is a diagram showing the protective effects of the inhibition of oxidative stress by inhaled hydrogen gas against ischemia-reperfusion injury and showing results of staining slices with TTC.
Figure 26:
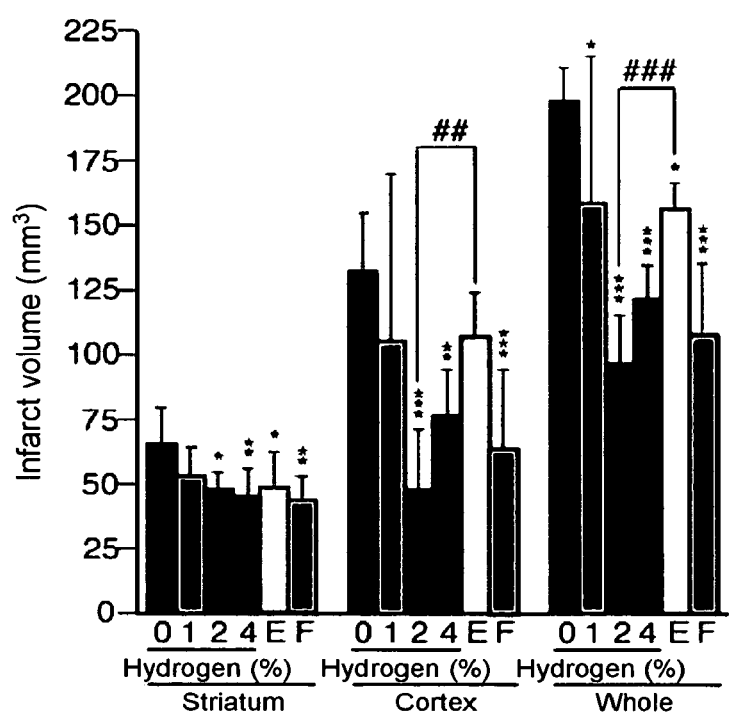
FIG. 26 is a graph showing the protective effects of the inhibition of oxidative stress by inhaled hydrogen gas against ischemia-reperfusion injury and showing a brain infarct volume.

An infarct volume was estimated by measuring visually white regions in the brain. The results are shown in FIGS. 25 and 26. FIG. 25 shows results of cutting the brain by coronal section into 6 slices after 1 day of mild cerebral artery occlusion and staining the slices with TTC. For comparison, two compounds were further tested. One of the compounds was Edaravone, which has been recommended in Japan to be used in the treatment of cerebral infarction. The other compound was FK506, which is under clinical trial for cerebral infarction in USA. The hydrogen molecules were more effective for the alleviation of an oxidative disorder than any of the other compounds tested. FIG. 26 shows a brain infarct volume. The brain infarct volume was calculated as a total sum of all the slices according to the equation: infarct area×thickness. The marks E and F in FIG. 26 denote infarct volumes from Edaravone (6 mg/kg of body weight) and FK506 (1 mg/kg of body weight), respectively, administered under the optimum conditions. An average value of infarct volumes and standard deviation were determined from the values of 6 animals in each group. *$P<0.05$, $P<0.01$, *$P<0.001$ as compared with a hydrogen gas concentration of 0%. ##$<0.01$, ###$P<0.001$ as compared with a hydrogen gas concentration of 2%.

Hydrogen concentration-dependent reductions in infarct volume were obviously observed, as shown in FIGS. 25 and 26, and the hydrogen concentration of 2% was most effective (FIG. 26).

Figure 27:
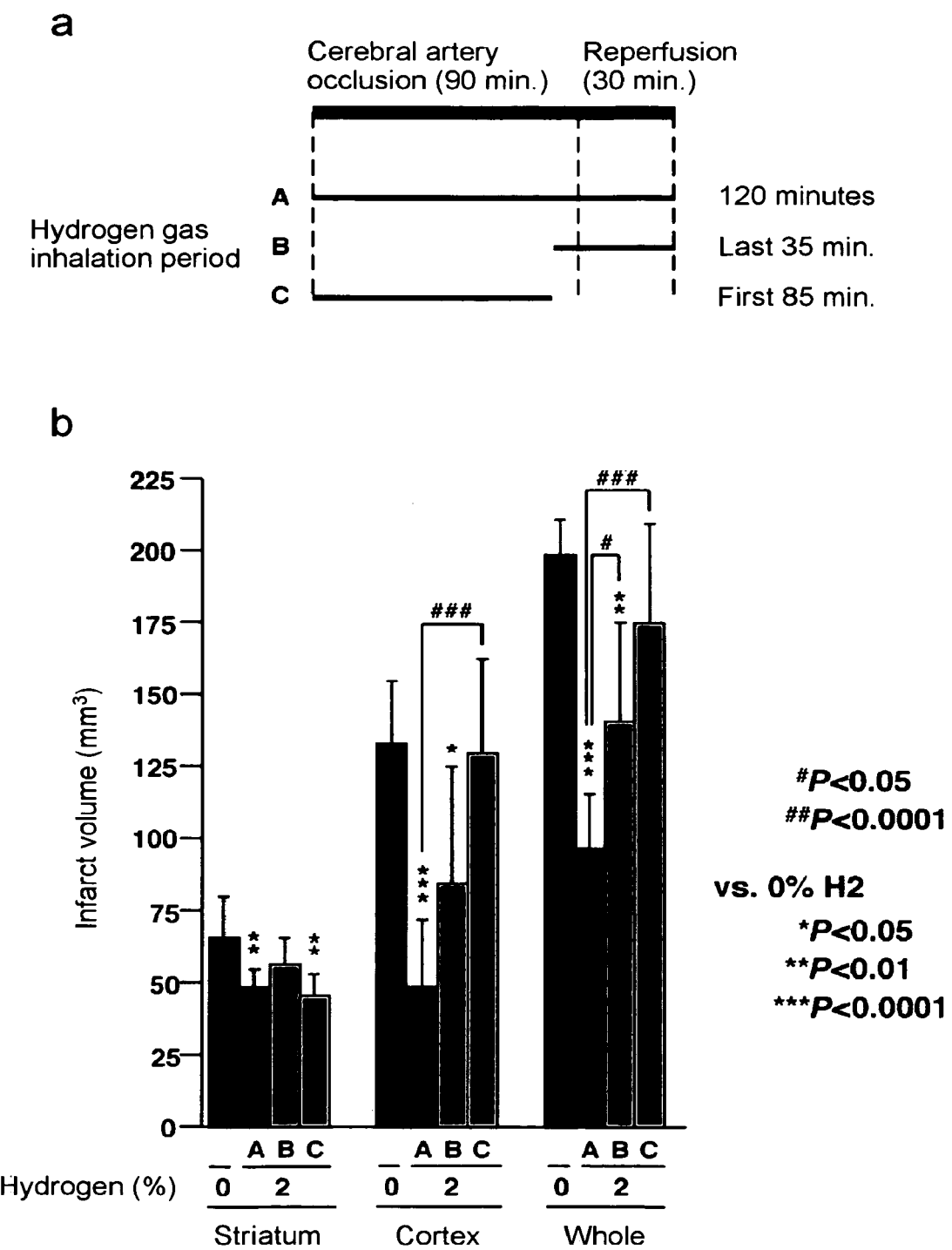
FIG. 27 is diagram and graph showing protective effects against ischemia-reperfusion injury in varying hydrogen gas inhalation periods.

FIG. 27 shows results of performing hydrogen inhalation only during ischemia but not during reperfusion. Rats were rendered locally ischemic for 90 minutes by mild cerebral artery occlusion and subsequently reperfused for 30 minutes. The rats inhaled 2% hydrogen gas in 3 different periods A, B, and C. FIG. 27a shows a schematic diagram thereof. FIG. 27b shows an infarct volume from hydrogen gas inhalation in the 3 different periods. The brain was cut by coronal section into 6 slices after 1 day of mild cerebral artery occlusion, and the slices were stained with TTC. The brain infarct volume was calculated as a total sum of all the slices according to the equation: infarct area×thickness. *$P<0.05$, $P<0.01$, *$P<0.0001$ as compared with a hydrogen gas concentration of 0%. #$P\ 0.05$, ###$P<0.0001$ as compared with the period A. The infarct volume is not reduced by performing hydrogen inhalation only during ischemia but not during reperfusion, as shown in FIG. 27. These results indicate that the hydrogen molecules must be present during reperfusion for exhibiting their protective effects.

Figure 28:
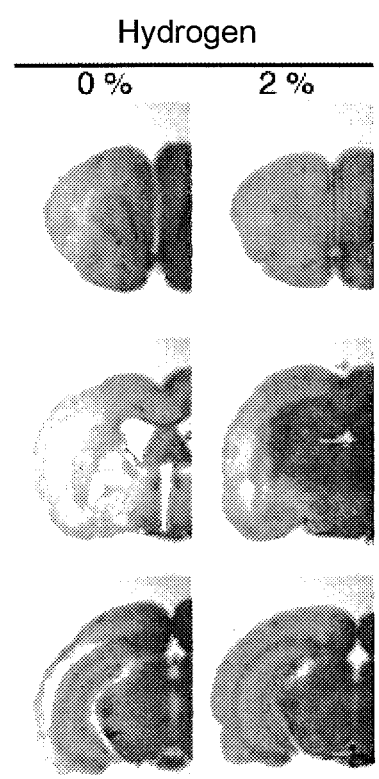
FIG. 28 is a diagram showing the protective effects of the inhibition of oxidative stress by inhaled hydrogen gas against ischemia-reperfusion injury and showing results of staining, with hematoxylin-eosin, brain coronal sections after one week.
Figure 29:
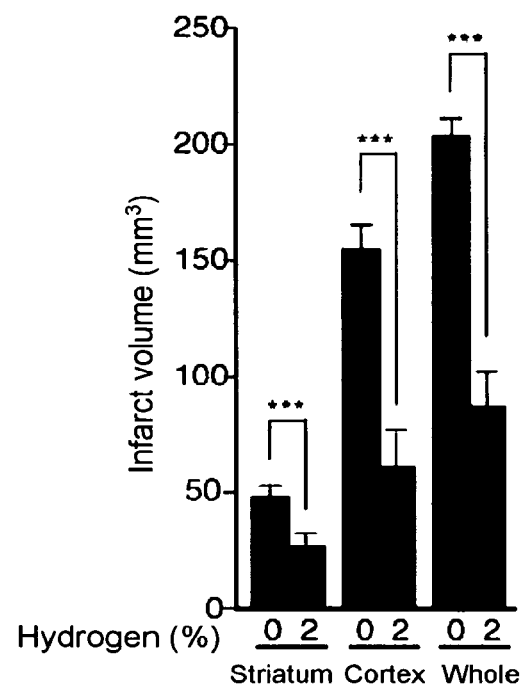
FIG. 29 is a graph showing the protective effects of the inhibition of oxidative stress by inhaled hydrogen gas against ischemia-reperfusion injury and showing results of calculating an infarct volume after one week, with a visually pale pink region obtained by hematoxylin-eosin staining as an infarction region.

Moreover, the difference in infarct volume between the hydrogen-treated group and the hydrogen-untreated group was more significant after 1 week of mild cerebral artery occlusion, as shown in FIGS. 28 and 29. FIG. 28 shows results of staining, with hematoxylin-eosin, brain slices obtained by coronal section after 1 week of mild cerebral artery occlusion. The photographs of FIG. 28 are the staining images of 3 different slices obtained by this method. FIG. 29 shows results of calculating an infarct volume in the same way as above, with a visually pale pink region obtained by hematoxylin-eosin staining as an infarction region. An average value of infarct volumes and standard deviation were determined from the values of 6 animals in each group. *$P<0.05$, $P<0.01$, *$P<0.001$.

Figure 30:
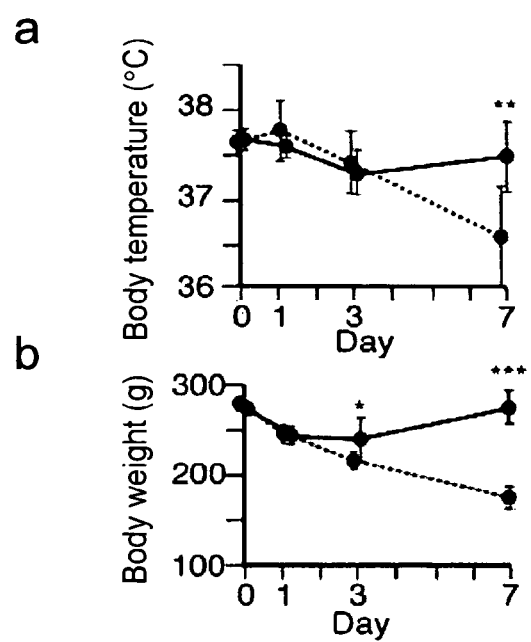
FIG. 30 is a graph showing changes in the body temperatures or body weights of hydrogen-treated or hydrogen-untreated rats.

The hydrogen-treated rats were observed to be improved both in body weight and in body temperature as compared with the hydrogen-untreated rats, as shown in FIG. 30. FIGS. 30a and 30b show changes in body temperature and in body weight, respectively, by 2% hydrogen gas inhalation (solid line) and non-inhalation (broken line). An average value and standard deviation were determined from the values of 6 animals in each group. *$P<0.05$, $P<0.01$, *$P<0.001$. As seen from these results, the hydrogen molecules not only alleviated an early brain disorder but also inhibited the progression of the disorder.

Figure 31:
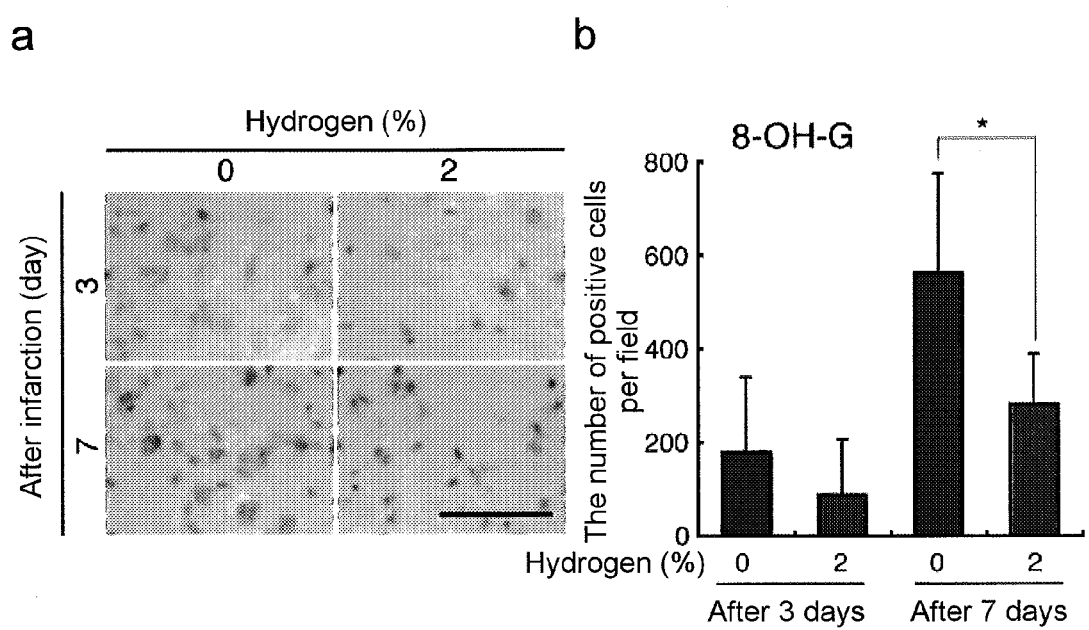
FIG. 31 is diagram and graph showing results of immunostaining the brain with anti-8-OH-G antibody after ischemia-reperfusion injury in the presence or absence of hydrogen gas.
Figure 32:
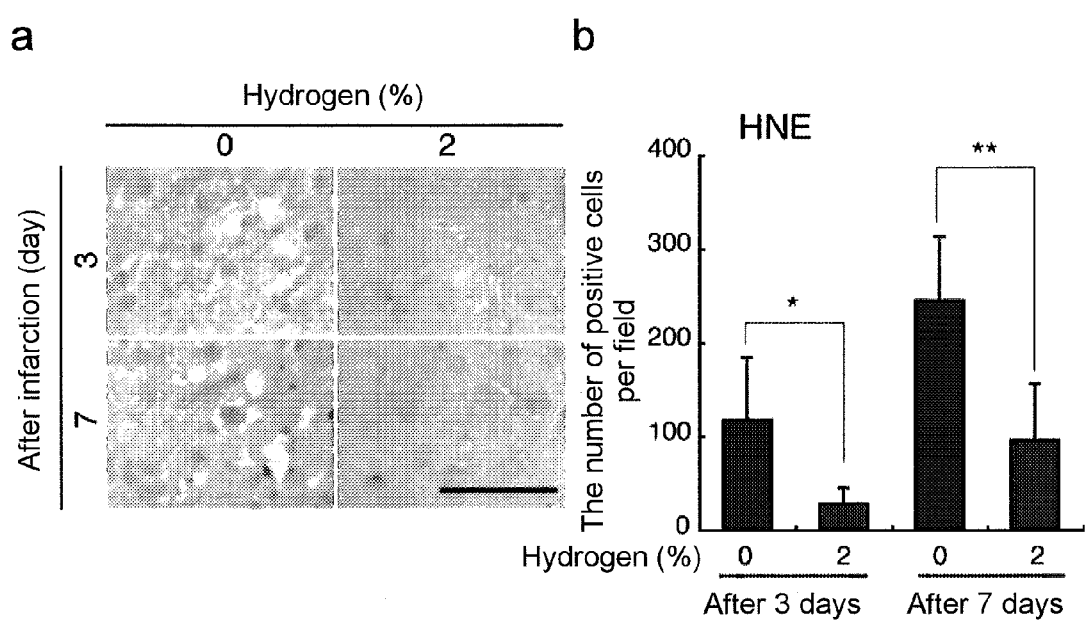
FIG. 32 is diagram and graph showing results of immunostaining the brain with anti-HNE antibody after ischemia-reperfusion injury in the presence or absence of hydrogen gas.
Figure 33:
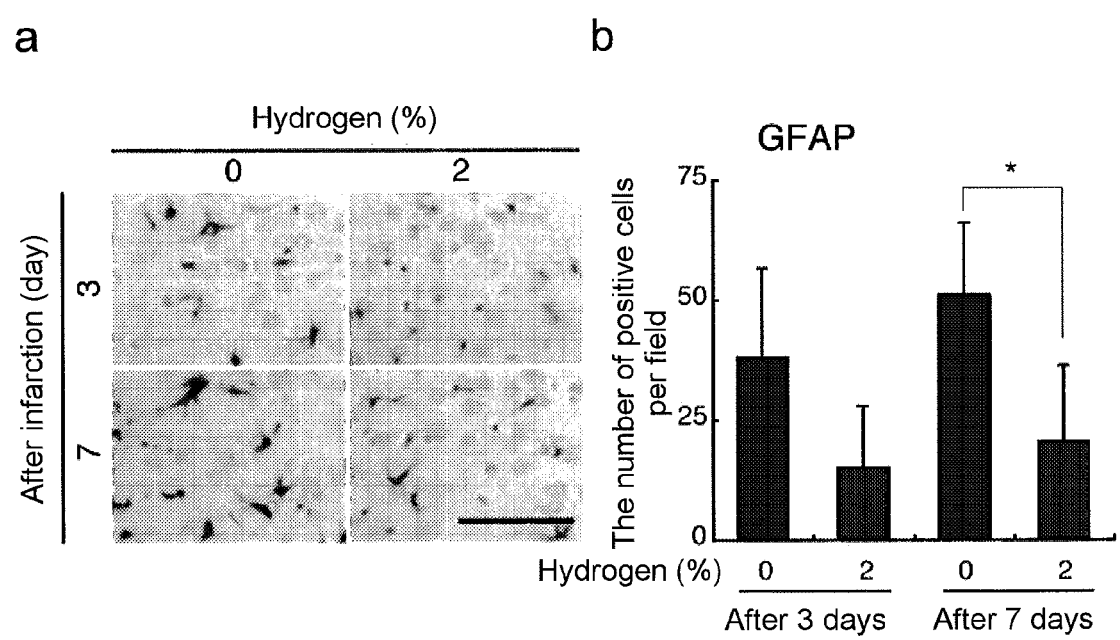
FIG. 33 is diagram and graph showing results of immunostaining the brain with anti-GFAP antibody after ischemia-reperfusion injury in the presence or absence of hydrogen gas.

Results of using the brain after 1 week of occlusion to examine changes produced at a molecular level by the protective effects of hydrogen molecules, by staining brain slices with anti-8-OH-G antibody indicating nucleic acid oxidation and anti-HNE antibody indicating lipid oxidation, and anti-GFAP antibody are shown in FIGS. 31 to 33. FIG. 31 shows the results obtained by using anti-8-OH-G antibody. FIG. 32 shows the results obtained by using anti-HNE antibody. FIG. 33 shows the results obtained by using astrocyte-specific anti-GFAP antibody. The brain was fixed after 3 days or 7 days of mild cerebral artery occlusion and embedded in paraffin. The coronal sections of 6 µm in thickness were stained with anti-8-OH-G, anti-HNE, or anti-GFAP antibodies. The left photographs of FIGS. 31 to 33 show the same regions adjacent to occlusion in the temporal cortical regions. The scale bar denotes 100 µm. The right graphs of FIGS. 31 to 33 show results of determining an average value of the number of cells positive to each antibody in a certain field (0.25 $mm^2$) and standard deviation from 6 animals in each group. *$P<0.05$, **$P<0.01$. In the hydrogen-treated rats, all the oxidation marker stainings were significantly reduced.

Figure 34:
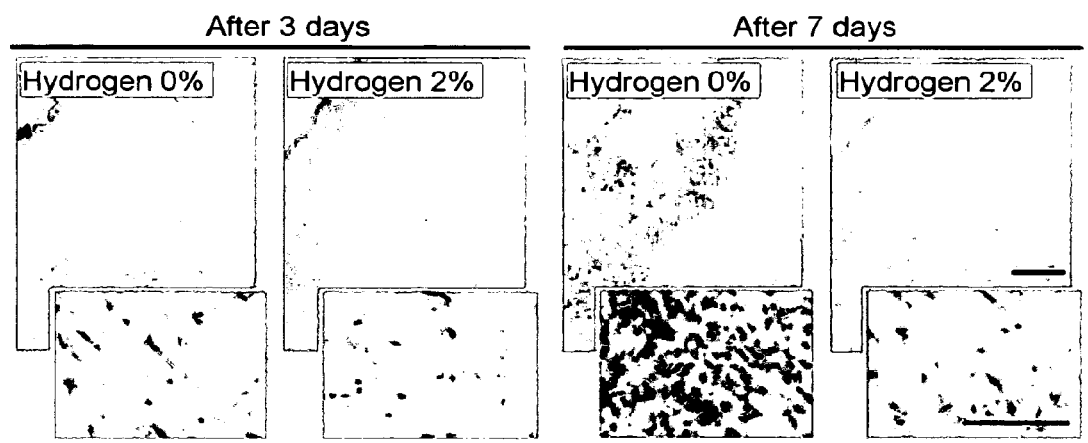
FIG. 34 is a diagram showing results of immunostaining the brain with microglia-specific anti-Iba-I antibody after ischemia-reperfusion injury in the presence or absence of hydrogen gas.
Figure 35:
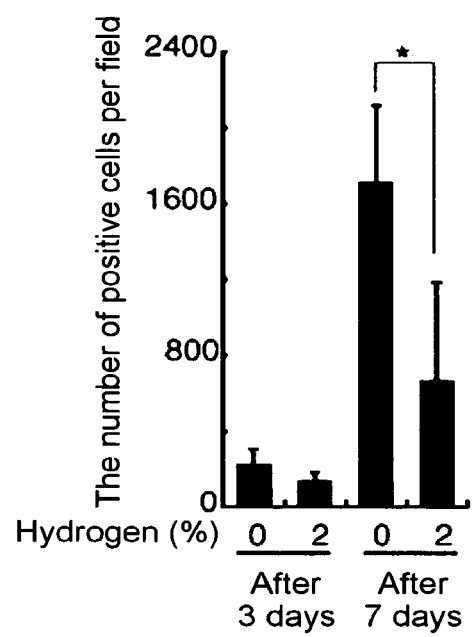
FIG. 35 is a graph showing the number of immunopositive cells as a result of staining the brain with microglia-specific anti-Iba-I antibody after ischemia-reperfusion injury in the presence or absence of hydrogen gas.

FIG. 34 shows results of staining the same brain regions with microglia-specific anti-Iba-I antibodies. In the staining experiment, the brain was fixed after 3 days or 7 days of mild cerebral artery occlusion and embedded in paraffin. The coronal sections were stained with each antibody. The photographs of FIG. 34 show the central regions of occlusion in the temporal cortical regions. The scale bar of FIG. 34 denotes 200 µm. The scale bar in the inserted photographs of FIG. 34 denotes 100 µm. In FIG. 35, an average value of the number of Iba-1-positive cells in a certain field and standard deviation were determined from 6 animals in each group. *$P<0.05$. The same brain regions were stained with microglia-specific anti-Iba-I antibodies, as shown in FIGS. 34 and 35. As a result, the staining with anti-Iba-I antibodies was significantly reduced by hydrogen treatment. Microglia accumulation serves as an indicator for a brain disorder. These results strongly suggest that the hydrogen molecules remarkably inhibit oxidative stress and further a brain disorder.

Example 18

Effects of Hydrogen Water

Increasing in SOD−/SOD−Homozygous Mouse Birth Rate of SOD Knockout Mice

Figure 37:
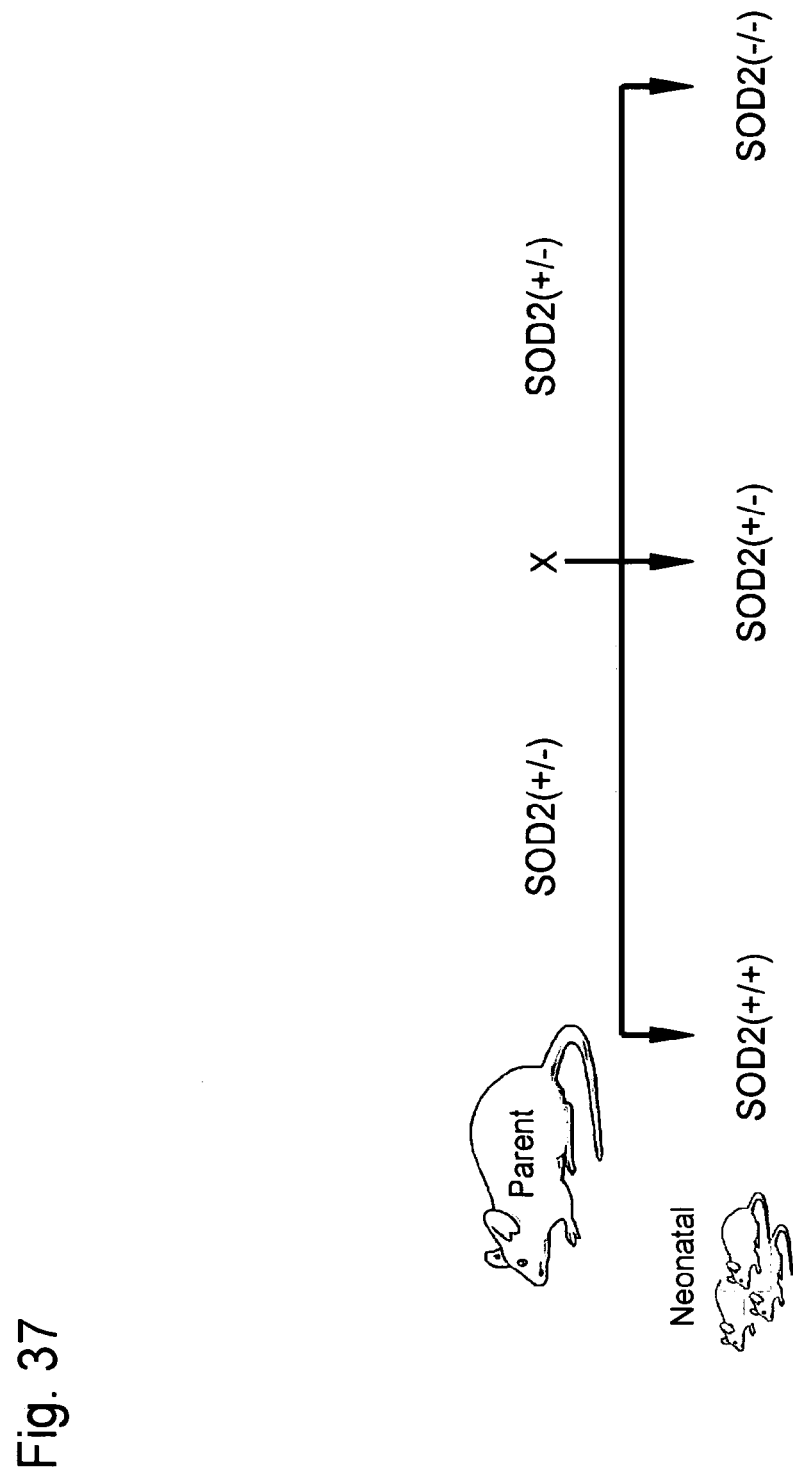
FIG. 37 is a diagram showing the genotypes of mice born by the crossing between SOD (+/−) mice.

MnSOD (manganese superoxide dismutase) present in mitochondria is an enzyme that converts superoxide ($O_2^-$.) generated within mitochondria to hydrogen peroxide. MnSOD gene is present in the nuclear genome. MnSOD deficiency accumulates $O_2^-$., which in turn reacts with NO with increased frequency and thereby increases harmful $ONOO^-$ (peroxynitrite) levels, causing cytotoxicity. Alternatively, $O_2^-$. reduces transition metals and increases $Cu^{2+}$ and $Fe^{2+}$ levels. Therefore, the accelerated Fenton reaction generates harmful hydroxyl radicals (.OH). Thus, an MnSOD-deficient animal birth rate is reduced due to stillbirth. Alternatively, MnSOD-deficient animals, even if born, die within 1 week. The crossing between mice heterozygously having MnSOD-deficient genes (SOD2 (+/−)) produces mice with normal MnSOD (SOD2 (+/+)), mice heterozygously having MnSOD (SOD2 (+/−)), and mice completely deficient in MnSOD (SOD (−/−)), which are supposed to be born at a 1:2:1 ratio according to the Mendel's laws. In reality, an MnSOD-deficient mouse birth rate is reduced due to stillbirth caused by the harmful active oxygen and free radicals (FIG. 37).

Sixteen female MnSOD heterozygous mice were divided into 2 groups. In one of the group, the mice drank hydrogen water for 8 days and were crossed. Then, the mice kept drinking hydrogen water until birth. These two groups resulted in 5 and 6 pregnant mice, respectively, from which 42 and 45 mice were born. DNA was extracted from the tails of these neonatal mice, and genotypes were determined according to a standard method.

Figure 38:
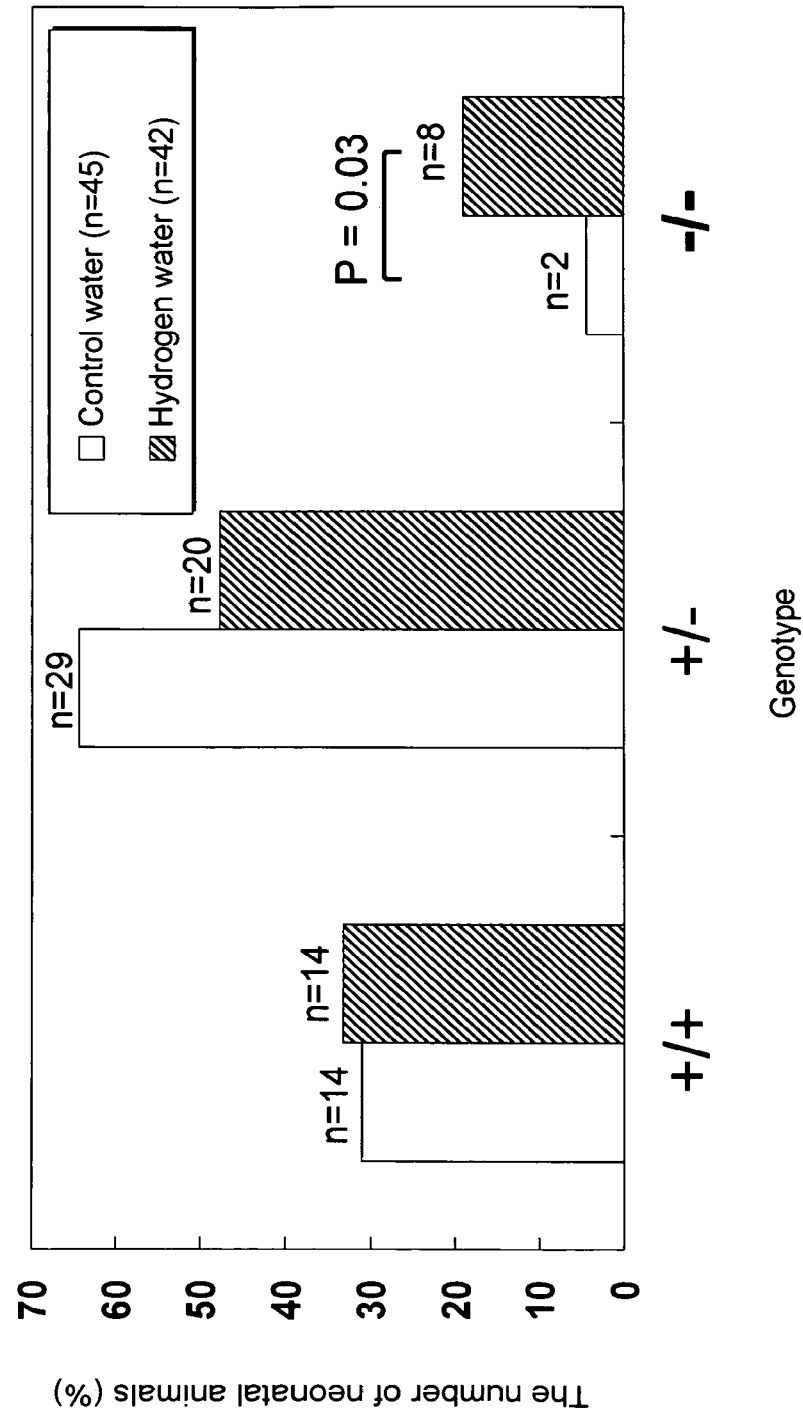
FIG. 38 is a graph showing the effects of hydrogen water on the genotypes of mice born by the crossing between SOD (+/−) mice.

The ratio of the 45 neonatal mice born from the mice that drank control water were MnSOD (+/+):MnSOD (+/−):MnSOD (−/−) of 14:29:2. On the other hand, the ratio of the 42 neonatal mice born from the mother mice that drank hydrogen water was 14:20:8. The number of the MnSOD (−/−) mice born was 8 times larger than that from the control mice and was statistically significant (FIG. 38).

These results demonstrate that the hydrogen water alleviates oxidative stress attributed to $O_2^-$..

Example 19

Carcinogenesis Inhibitory Effects of Drinking and Intraperitoneal Administration of Hydrogen Water Various medium-term carcinogenicity assays have been developed in recent years as a detection method for predicting carcinogenicity. The assays involve: first administering, to two-stage carcinogenesis models prepared with rodents, known carcinogens for initiation treatment in an amount that is small enough not to cause cancer; then administering a test substance thereto, and detecting the presence or absence of promotion effects. To detect carcinogenicity, the carcinogenicity of the test subject is evaluated with attention focused particularly on the promotion effects.

A medium-term liver carcinogenicity assay (Ito test) is a method involving: conducting partial hepatectomy at the early stage during the promotion stage; and promoting liver cell division at the regenerative proliferation stage to thereby induce mutant cell foci in a short time. This assay has allegedly accumulated the greatest deal of data to this day (Ito N, Tamano S, Shirai T., Cancer Sci. 2003 January; 94 (1): 3-8. Review). The assay is targeted for the rat liver. Among 313 chemicals already detected in this assay, 60/65 (92%) chemicals regarded as hepatocarcinogens (including promoters) have been reported to give positive results. This assay has been said to be a highly reliable and useful detection method for detecting carcinogens targeted for the liver. Furthermore, the results of detecting hepatocarcinogens at varying administration doses by this assay correlates, as to the quantified value of formation of GST-P-positive cell foci, with the results of hepatocellular carcinoma incidence shown by long-term carcinogenicity assay. Moreover, dose correlation has also been reported (Ogiso, T. et al., Toxicol. Pathol., 13, 257-265, 1985).

In this Example, a detection method was used wherein MeIQx that is one of heterocyclic amines and has been reported to have liver carcinogenicity was administered simultaneously with a test substance at the promotion stage of the medium-term liver carcinogenicity assay. This detection method has been developed to detect the inhibitory effects of a test substance on liver carcinogenesis. Hirose et al. (Hirose, M. et al., Carcinogenesis, 16, 3049-3055, 1995) have previously found some liver carcinogenesis inhibitors by use of this model.

In this Example, the test substances used were a hydrogen-containing saline ($H_2$ saline) and hydrogen-containing water ($H_2$ water). In this Example, the models were used to detect the liver carcinogenesis inhibitory effects of the intraperitoneal administration of the hydrogen-containing saline as a test substance and the additional administration of the hydrogen-containing water by drinking.

For the purpose of examining the presence or absence of the liver carcinogenesis inhibitory effects of combined administrations of the hydrogen-containing saline and the hydrogen-containing water, the medium-term liver carcinogenicity assay using placental Glutathione S-transferase (GST-P)-positive cell foci as an indicator was used to conduct quantitative study.

Figure 39:
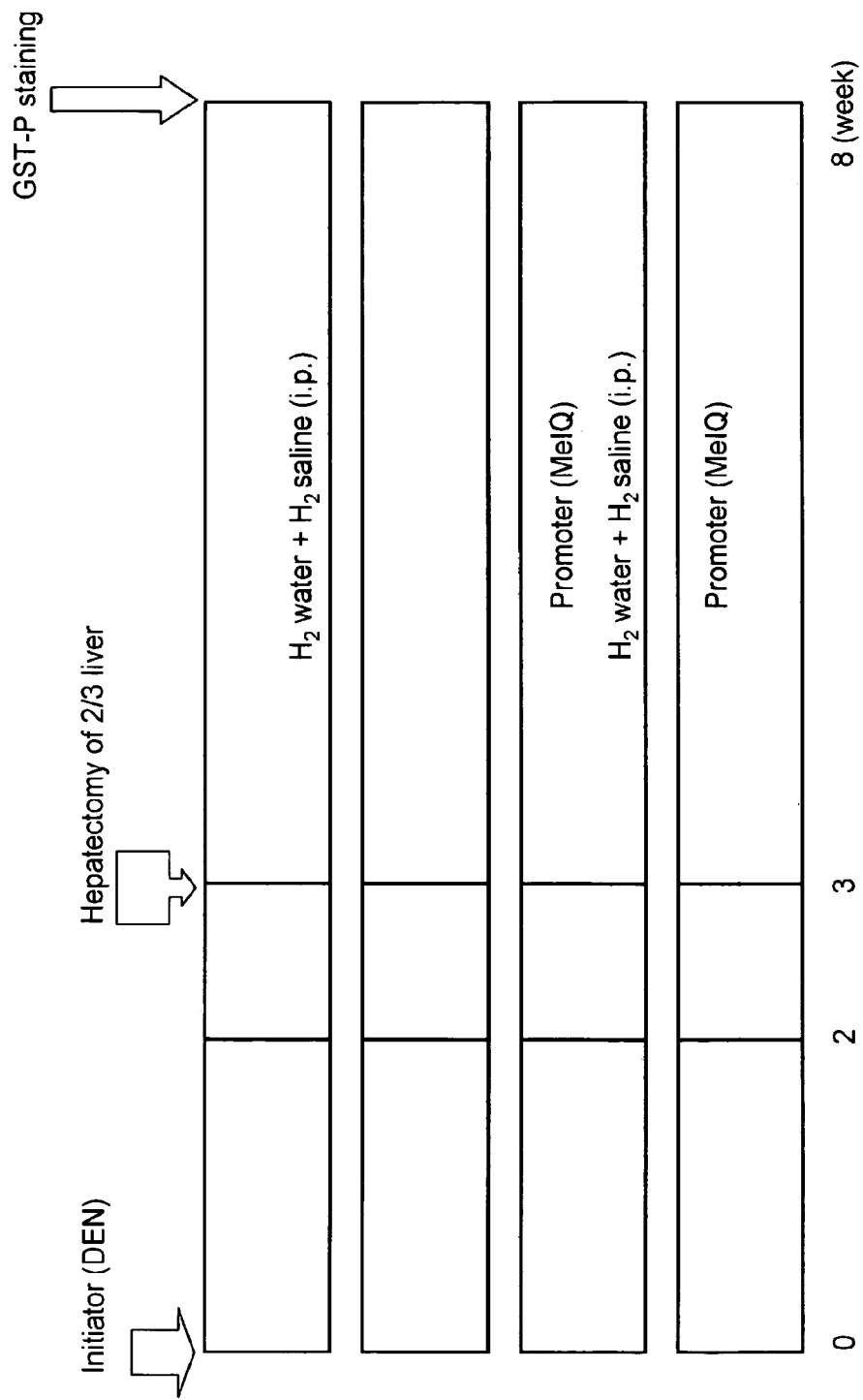
FIG. 39 is a diagram showing an experimental method for evaluating the carcinogenesis inhibitory effects of hydrogen water.

Six-week-old male F334 rats received: the single intraperitoneal administration of Diethylnitrosamine (DEN) as an initiator at a dose of 200 mg/kg for initiation treatment of liver carcinogenesis; 6-week intraperitoneal administration starting 2 weeks thereafter, wherein the hydrogen-containing saline as a test substance at a dose of 10 ml/kg was administered as frequently as twice a day or seven times a week; and the additional administration of the hydrogen-containing water by drinking. A control group received the intraperitoneal administration of a saline and the administration of tap water by drinking. Moreover, a DEN-untreated control group and a test substance-administered group were also provided. Each of the DEN-treated and DEN-untreated groups was further subdivided into a group that received the 6-week combined administration of the test substance with a hepatocarcinogen 2-amino-3,8-dimethylimidazo[4,5-f]quinoxaline (MeIQx) as a promoter at a concentration of 0.02% in feed. After a lapse of the 3rd week of the experiment (after 1 week of initiation of test substance administration), partial hepatectomy was conducted on all the animals. After a lapse of 8 weeks from the initiation of the experiment (after the completion of the test substance administration period), the animals were slaughtered and autopsied. Then, quantitative analysis was conducted on GST-P-positive cell foci in the liver. FIG. 39 shows the experimental method.

Changes in general state attributed to test substance administration, dead animals, and changes in body weight were not observed during the administration period. The amount of water ingested exhibited high value tendency in all the test substance-administered groups for a period of time in the administration period. Thus, this tendency was probably brought by the influence of test substance administration.

In liver weight and visual pathologic investigations, the influence of test substance administration was not observed. In biochemical blood examination as well, changes suggesting the toxicity of test substance administration were not observed. The test substance used here presumably inhibits lipid peroxide generation. Thus, measurement was also performed as to serum lipid peroxide. However, such inhibition was not observed in the experiment performed here.

FIG. 40 shows results of measuring the number of GST-P-positive cell foci in the liver (FIG. 40a) and the areas of the positive foci (FIG. 40b). The combined administration of the hydrogen-containing saline (administered intraperitoneally) and the hydrogen-containing water (administered by drinking) inhibited, albeit moderately, the formation of GST-P-positive cell foci in the DEN-treated group. The inhibition rate thereof was 28.0% for the number and 25.2% for the area. Moreover, the hydrogen-containing saline and the hydrogen-containing water also inhibited, albeit moderately, the formation of GST-P-positive cell foci in the group that received the administration of MeIQx in addition to DEN. The inhibition rate thereof was 21.0% for the number and 20.9% for the area.

Thus, the hydrogen-containing saline and the hydrogen-containing water were effective for the inhibition of carcinogenesis.

INDUSTRIAL APPLICABILITY

The present invention comprises the constitution described above. As a result, the present invention, as described in detail in Examples below, can eliminate in vivo harmful reactive oxygen species and/or free radicals and can therefore suppress various adverse effects attributed to the presence of this reactive oxygen species and/or free radicals. Thus, the present invention exhibits such excellent effects that it can contribute to the suppression of human aging process, health promotion, and the prevention of disease. The results of Examples described later demonstrate that hydrogen molecules have many advantages as an effective antioxidant. Specifically, the hydrogen molecules effectively scavenge .OH at appropriate strength that does not influence reactive oxygen species in metabolic oxidation-reduction reactions or cell signaling. Many known antioxidants cannot easily reach target organelles or tissues. By contrast, the hydrogen molecules have the property of easily passing through biomembranes and being effectively distributed in cytoplasm by diffusion. Oxidative stress caused by inflammation or ischemia-reperfusion is also caused by other various circumstances. Examples thereof include excessive exercise, myocardial infarction, operations stopped due to bleeding, and organ transplantation. Antioxidants that are so effective yet non-damaging, such as hydrogen molecules, are applicable in many medical fields by virtue of their convenience. Hydrogen gas inhalation has already been used for protecting divers from caisson disease caused by reduced pressure, and their safety has been confirmed widely. Moreover, hydrogen concentrations used in treatment according to the present invention are in no danger of fires or explosion. Furthermore, inhaled hydrogen gas is dissolved in liquids and easily transferred through blood vessels. Thus, hydrogen, one of the most well known molecules, is widely applicable as a safe and effective antioxidant with few side effects in medical fields.

All publications, patents, and patent applications cited herein are incorporated herein by reference in their entirety.

The invention claimed is:

1. A method of treating ischemia-reperfusion injury attributed to reactive oxygen species and/or free radicals caused by blood flow being stopped and then restarted during a surgery on a patient, which comprises administering a gas comprising hydrogen molecules as an active ingredient to the patient, wherein the hydrogen molecules are present in the patient during reperfusion and wherein the gas comprising hydrogen molecules comprises hydrogen gas at a concentration of 1 to 4% (v/v).

2. The method according to claim 1, wherein the reactive oxygen species and/or free radicals are hydroxyl radicals or peroxynitrite.

3. The method according to claim 1, wherein the gas comprising hydrogen molecules comprises a mixed gas of hydrogen gas and oxygen gas.

4. The method according to claim 1, wherein the gas comprising hydrogen molecules comprises a mixed gas of hydrogen gas, oxygen gas, and inert gas.

5. The method according to claim 1, wherein the gas comprising hydrogen molecules comprises a mixed gas of hydrogen gas and air.

6. The method according to claim 1, wherein the gas comprising hydrogen molecules comprises a mixed gas of hydrogen gas and anesthetic gas.

7. A method of treating ischemia-reperfusion injury attributed to reactive oxygen species and/or free radicals caused by blood flow being stopped and then restarted during a surgery on a patient, which comprises administering a gas comprising hydrogen molecules as an active ingredient to the patient, wherein the hydrogen molecules are present in the patient during reperfusion and wherein the gas comprising hydrogen molecules comprises hydrogen gas at a concentration of 1.0 to 4.5% (v/v).

* * * * *